(12) United States Patent
Djokic

(10) Patent No.: US 7,687,076 B2
(45) Date of Patent: Mar. 30, 2010

(54) DEPOSITION PRODUCTS, COMPOSITE MATERIALS AND PROCESSES FOR THE PRODUCTION THEREOF

(75) Inventor: Stojan Djokic, Edmonton (CA)

(73) Assignee: Exciton Technologies Inc. (CA)

(*) Notice: Subject to any disclaimer, the term of this patent is extended or adjusted under 35 U.S.C. 154(b) by 389 days.

(21) Appl. No.: 11/934,459

(22) Filed: Nov. 2, 2007

(65) Prior Publication Data

US 2008/0075650 A1 Mar. 27, 2008

Related U.S. Application Data

(63) Continuation of application No. 10/830,574, filed on Apr. 23, 2004, now Pat. No. 7,300,673.

(30) Foreign Application Priority Data

May 16, 2003 (CA) .................................. 2428922
Mar. 10, 2004 (CA) .................................. 2460585

(51) Int. Cl.
| | |
|---|---|
| A61K 33/38 | (2006.01) |
| A61K 9/70 | (2006.01) |
| A61K 33/40 | (2006.01) |
| A61K 33/04 | (2006.01) |
| A61K 31/28 | (2006.01) |
| A61K 31/10 | (2006.01) |
| A61L 15/00 | (2006.01) |
| A01N 39/00 | (2006.01) |
| A01N 59/16 | (2006.01) |
| A01N 59/02 | (2006.01) |
| A01N 55/02 | (2006.01) |
| A01N 41/10 | (2006.01) |

(52) U.S. Cl. .................. 424/618; 424/443; 424/445; 424/613; 424/703; 514/495; 514/709

(58) Field of Classification Search .................. None
See application file for complete search history.

(56) References Cited

U.S. PATENT DOCUMENTS

| | | | |
|---|---|---|---|
| 4,297,249 A * | 10/1981 | Przybyla et al. ......... 252/62.3 R |
| 4,728,323 A | 3/1988 | Matson |
| 5,098,582 A | 3/1992 | Antelman |
| 5,211,855 A | 5/1993 | Antelman |
| 5,372,847 A | 12/1994 | Silver et al. |
| 5,413,788 A | 5/1995 | Edwards et al. |
| 5,474,797 A | 12/1995 | Sioshansi et al. |
| 5,676,977 A | 10/1997 | Antelman |
| 5,681,575 A | 10/1997 | Burrell et al. |
| 5,814,094 A | 9/1998 | Becker et al. |
| 5,928,174 A | 7/1999 | Gibbins |
| 5,985,308 A | 11/1999 | Burrell et al. |
| 6,017,553 A | 1/2000 | Burrell et al. |
| 6,080,490 A | 6/2000 | Burrell et al. |
| 6,087,549 A | 7/2000 | Flick |
| 6,224,983 B1 | 5/2001 | Sodervall et al. |
| 6,238,686 B1 | 5/2001 | Burrell et al. |
| 6,267,782 B1 | 7/2001 | Ogle et al. |
| 6,306,341 B1 | 10/2001 | Yokota et al. |
| 6,333,093 B1 | 12/2001 | Burrell et al. |
| 6,355,858 B1 | 3/2002 | Gibbins |
| 6,379,712 B1 | 4/2002 | Yan et al. |
| 6,426,195 B1 | 7/2002 | Zhong et al. |
| 6,436,420 B1 | 8/2002 | Antelman |
| 6,444,109 B1 * | 9/2002 | Redline et al. ............ 205/85 |
| 2001/0009831 A1 | 7/2001 | Schink et al. |
| 2001/0024662 A1 | 9/2001 | Yang |
| 2002/0051824 A1 | 5/2002 | Burrell et al. |
| 2002/0127282 A1 | 9/2002 | Antelman |

FOREIGN PATENT DOCUMENTS

| | | |
|---|---|---|
| CA | 0875146 A1 | 4/1998 |
| CA | 2102433 | 3/2000 |
| CN | 1149389 | 5/1997 |
| GB | 431656 | 7/1935 |
| WO | WO2004037187 A2 | 5/2004 |

OTHER PUBLICATIONS

N.R. Thompson, Silver, in Comprehensive Inorganic Chemistry, v.IIID, J.C. Bailer et al, Editors, Pergamon Press (1973) 79-82.
K.J. Bundy et al, "An Investigation of the Bacteriostatic Properties of pure Metals", Journal of Biomedical Materials Research, v. 14 (1980) 653-662.
D. Acel, "Uber die oligodynamishe Wirkung der Metalle," Z. Biochem, 112 (1920) 23-26 with English Abstract.
J. Gibbard, "Public Health Aspects of the Treatment of Water and Beverages with Silver", Journal of American Public Health, v. 27 (1937) 112-11.
S.S. Djokic and R.E. Burrell, "Behavior of Silver in Physiological Solutions", Journal of Electrochemical Society, v. 145 (5) (1998) 1426-1430.
S.S. Djokic et al, "An Electrochemical Analysis of Thin Silver Produced by Reactive Sputtering", J. of Electrochemical Society v. 148(3) (2001) C191-C196.
C.L. Fox, "Topical Therapy and the Development of Sulfadiazine", Surgery, Gynecology & Obstetrics, 157 (1983) 82-88.

(Continued)

Primary Examiner—Ernst V Arnold
(74) Attorney, Agent, or Firm—Terrence N. Kuharchuk; Rodman & Rodman

(57) ABSTRACT

A method for producing a deposition product includes providing a deposition solution having a pH below 7 and comprising an aqueous solution of a silver salt comprised of silver ions and an oxidizing agent. The silver salt is comprised of silver nitrate and has a concentration in the deposition solution between about 1 and 20 grams per liter. The oxidizing agent is comprised of a persulfate and has a concentration in the deposition solution between about 1 and 50 grams per liter. The method further includes producing the deposition product by facilitating a chemical reaction between the silver ions and the oxidizing agent while maintaining the deposition solution at a temperature of between about 2 and 40 degrees Celsius. The deposition product consists essentially of at least one oxidized silver species, and is comprised of a compound having the formula $Ag_7O_8X$, where X is an anion.

16 Claims, 14 Drawing Sheets

OTHER PUBLICATIONS

M.C. Fung, D.L. Bowen, "Silver Products for Medical Indications: Risk-Benefit Assessment", Clinical Toxicology, v. 34 (1) (1996) 119-126.

H.W. Margaf, T.H. Covey, "A Trial of Silver-Zinc-Allantoinate in the Treatment of Leg Ulcers", Arch. Surg. v. 112 (1977) 699-704.

S.I. Zhdanov, "Sulfur, Selenium, Tellurium and Polonium", in Standard Potentials in Aqueous Solutions, A.J. Bard et al, Editors, Marcel Dekker Inc., New York (1985) 93, 5pp.

M.S. Skanavi-Grigoreva, I.L. Shimanovich, Zh. Obsh., Khim., 24, (1954) 1490-1495 with English abstract.

"Electrocrystallization" article from website: www.mpi-stuttgart.mpg.de/jansen/p110, 2pp.

Leibecki, Harold F., "Argentic Oxysalt Electrodes", NASA Technical Note NASA TN D-3208, Washington, D.C., Jan. 1966.

McMillan, J.A., "Higher Oxidation of States of Silver", Chem. Rev. (Washington D.C.) 62, 1962, pp. 65-80.

Discussion Section, Journal of The Electrochemical Society, vol. 106, No. 12, Dec. 1959, pp. 1072-1084.

* cited by examiner

FIGURE 6(b)
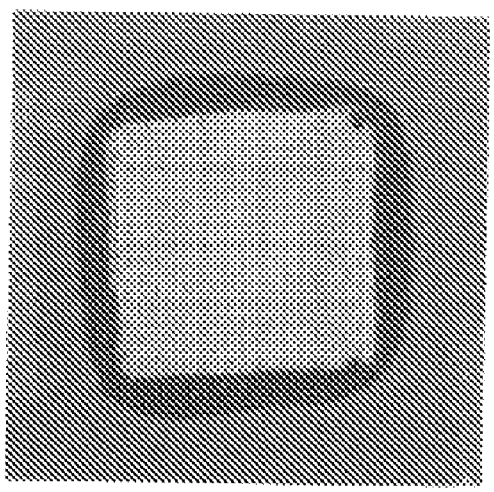
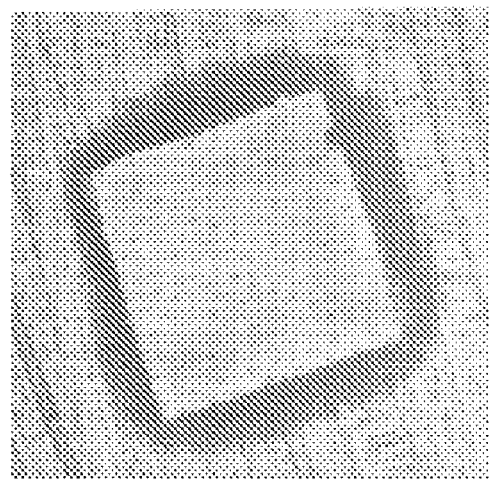
FIGURE 6(c)
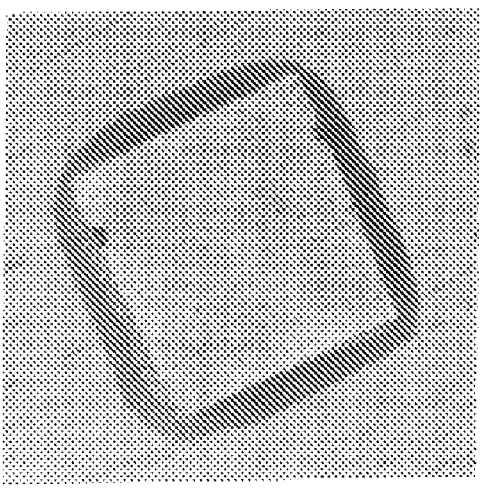
FIGURE 6(a)

DEPOSITION PRODUCTS, COMPOSITE MATERIALS AND PROCESSES FOR THE PRODUCTION THEREOF

FIELD OF INVENTION

Deposition products, composite materials including deposition products, and methods for producing the deposition products and the composite materials.

BACKGROUND ART

The germicidal properties of silver, even not known as such, have been utilized since the early Mediterranean cultures. It has been known since 1000 BC and possibly before that water kept in silver vessels and then exposed to light and filtered could be rendered potable. Other forms of silver have been used throughout centuries for various applications, such as coatings for prevention of beverages from spoilage or silver plates and foils in the surgical treatments of wounds and broken bones.

The lethal effects of metals towards bacteria and lower life forms were first scientifically described by von Nageli in the late nineteenth century, and this phenomenon has been defined as an "oligodynamic effect" (N. R. Thompson, Silver, in Comprehensive Inorganic Chemistry, Vol. III D, J. C. Bailer, H. J. Emeléus, R. Nyholm and A. F. Trutman-Dickenson, Editors, Pergamon Press, Oxford (1973)). The term oligodynamic effect is typically restricted to describing solutions in which the metal concentration is several orders of magnitude lower than that which would be lethal to higher organisms.

The investigation of the bacteriostatic properties of pure metals such as Fe, Mo, Cu, V, Sn, W, Au, Al, Ta, Nb, Ti, Zr, Ni, Co, Ag and Cr, has proved that Co was the only element which was inhibitory for the bacterial growth under anaerobic conditions (K. J. Bundy, M. F. Butler and R. F. Hochman, "An Investigation of the Bacteriostatic Properties of Pure Metals", Journal of Biomedical Materials Research, Vol. 14 (1980) 653-663). Under aerobic conditions both Cu and Co consistently display inhibitory effects. Some antimicrobial effects have been seen for Ni, Fe and V. However, other metals such as Mo, W, Al, Nb, Zr, Cr and most importantly for the present invention Ag and Sn never showed any tendency to inhibit the growth of *Streptococcus mutans*.

In the case of silver metal, it was in 1920, when Acél who was the first to attribute the antimicrobial properties of silver to the liberation of $Ag^+$ ions from the material (D. Acél, "Über die oligodynamische Wirkung der Metalle", Z. Biochem., 112 (1920) 23).

Gibbard reported in 1937 that pure metallic silver has no antimicrobial activity (J. Gibbard, "Public Health Aspects of the Treatment of Water and Beverages with Silver", Journal of American Public Health, Vol. 27 (1937) 112-119). His experiments showed that if silver is cleaned mechanically with an abrasive cloth or paper it becomes inactive. Similarly, if molten silver is allowed to cool in a reduction atmosphere (e.g. hydrogen), no antimicrobial activity is found. When cooling of molten silver is carried out in air, and formation of surface oxide occurred, an antimicrobial activity may be observed. Similar results were found when silver metal was treated with nitric acid in an air atmosphere (dissolution and formation of an oxide layer). Based on Gibbard's results, pure silver was devoid of activity, but surface oxidized silver was active. Silver oxide, silver nitrate and silver chloride were always active. Also, Gibbard observed that the antimicrobial properties of silver and its compounds were reduced in the presence of proteins or glucose.

Djokić investigated the behavior of silver films, e.g. physical vapor deposited, electrodeposited, electroless deposited and metallurgical in physiological saline solutions (S. S. Djokić and R. E. Burrell, "Behavior of Silver in Physiological Solutions", Journal of the Electrochemical Society, Vol. 145 (5) (1998) 1426-1430). Djokić found that an essential factor leading to an antimicrobial activity of metallic silver is a presence of Ag oxide(s) at the surface of this material. It was demonstrated that only silver films containing silver oxides (most likely $Ag_2O$) showed an antimicrobial activity. The behavior was attributed to the dissolution of $Ag_2O$ from the "silver" material and formation of $Ag^+$ or other complexed ions which become antimicrobially active. There was no evidence that pure metallic silver, no matter which way it was produced i.e., physical vapor deposited, electrodeposited or electroless deposited could be dissolved in physiological media, or that these materials would exhibit antimicrobial activity.

It should be noted that when the physical vapor deposition of silver was carried out in an atmosphere containing oxygen the resulted product, as found by the XRD analysis contained silver oxide. Consequently, these samples exhibited antimicrobial activity. Conversely, when the physical vapor deposition was carried out from an argon atmosphere (no presence of oxygen) pure metallic, nanocrystalline silver film was deposited as confirmed by the XRD analysis. However, these films did not dissolve in physiological saline solutions, nor they exhibited antimicrobial activity at all.

For an in depth understanding of structural properties of silver films produced by reactive sputtering, see Djokić et al. (S. S. Djokić, R. E. Burrell, N. Le and D. J. Field, "An Electrochemical Analysis of Thin Silver Produced by Reactive Sputtering", Journal of the Electrochemical Society, Vol. 148 (3) (2001) C191-C196.). To prove the concept that only oxidized silver species are responsible for the antimicrobial activity, Djokić further oxidized pure metallic silver samples (i.e. those produced by the electrodeposition, electroless deposition, physical vapor deposition in an argon atmosphere or metallurgically). The oxidation of these samples was carried out electrochemically in 1 M KOH solutions, using a process very well established in the art. The electrochemically oxidized silver samples were tested for the antimicrobial activity against *Pseudomonas aeruginosa*. Clear evidence was found that the electrochemically oxidized silver samples exhibited antimicrobial activity.

The above referenced work shows that only oxidized silver species, but not elemental silver will affect antimicrobial activity. The findings to date show that the "nanocrystalline" or "macrocrystalline" elemental silver does not have antimicrobial activity at all. Elemental silver, either nanocrystalline or "macrocrystalline" may exhibit some antimicrobial activity only if oxidized silver species are present at these surfaces or within the silver metal. Only the formation of silver oxide(s), carbonates or other silver salts (except silver sulfide, due to its extremely low solubility) at the surface or within the material, which may be influenced by an exposure of elemental silver to various bases, acids or due to atmospheric corrosion may lead to an antimicrobial activity of this material.

The use of silver on chronic wounds dates back in the $17^{th}$ and $18^{th}$ centuries. In the early $19^{th}$ century, silver nitrate began to be used on burns and in opthalmology. Concentrations of the solution ranged from 0.20 to 2.5 wt. % with the weaker solutions being reserved for children. Silver has been found to be active against a wide range of bacterial, fungal and viral pathogens. Topical treatment of acute and chronic wounds is a preferred and selective approach to the prevention of infection and healing. In order to achieve these requirements products that are used in the prevention of infections must have certain physical and chemical properties.

When used for topical dressings, silver compounds must have relatively low solubility. This is usually achieved by choosing compounds with a relatively low solubility products (e.g. $AgCl$, $Ag_2SO_4$, $Ag_2CO_3$, $Ag_3PO_4$, Ag-oxides). Kinetics of dissolution of these compounds in neutral aqueous solutions is quite slow. This property is very convenient for two reasons. First, a sustained release of silver ions from the silver compounds is more likely to provide a prolonged antimicrobial activity. Second, low amounts of the silver ions released into wound exudates may not give rise to transient high tissue blood and urine levels, thus avoiding systemic toxicity. The choice of a particular silver compound will depend upon its reactivity with wound exudates. This reactivity should preferably be minimized in order to achieve the desired effect of the released silver ions (i.e., antimicrobial activity without systemic toxicity).

Besides silver nitrate, one of the most widely used topical antimicrobial materials is silver sulfadiazine (C. L. Fox, "Topical Therapy and the development of Silver Sulfadiazine", Surgery, Gynecology & Obstetrics, 157 (1) (1983) 82-88). This compound is synthesized from silver nitrate and sodium sulfadiazine. Silver sulfadiazine has been used in treatments of burns, leg ulcers and also as a topical antimicrobial agent in the management of infected wounds.

Products such as silver protein (argyrols) or mild silver protein are mixtures of silver nitrate, sodium hydroxide and gelatin. These products are recommended for internal use and are promoted as essential mineral supplements. Although there is no theoretical or practical justification for their use, this class of compounds has been recommended for the treatment of diverse diseases such as cancer, diabetes, AIDS and herpes (M. C. Fung, D. L. Bowen, "Silver Products for Medical Indications: Risk—Benefit Assessment", Clinical Toxicology, Vol. 34 (1) (1996) 119-126).

Silver-zinc-allantoinate has been formulated as a cream and represents a combination of silver, zinc and allantoin (an agent that stimulates debridement and tissue growth (H. W. Margaf, T. H. Covey, "A Trial of Silver-Zinc-Allantoinate in the Treatment of Leg Ulcers", Arch. Surg., Vol. 112 (1977) 699-704). This composition exhibited promising effects in preliminary studies.

In the past few decades several topical dressings containing silver have been developed for wound care. Such materials include Arglaes™, Silverlon™, Acticoat™, Actisorb™, and Silver 220™.

Antimicrobial coatings and methods of forming same are the subject of U.S. Pat. No. 5,681,575 (Burrell et al) and U.S. Pat. No. 6,238,686 (Burrell et al). The coatings are formed by the physical vapour deposition of biocompatible metal and the preferred biocompatible metal is silver.

Burrell et al teach that atomic disorder may be created in metal powders or foils by cold working and in metal coatings by depositing by vapor deposition at low substrate temperatures and that such metal coatings constitute a matrix containing atoms or molecules of a different material. The presence of different atoms or molecules results in atomic disorder in the metal matrix, for instance due to different sized atoms. The different atoms or molecules may be one or more second metals, metal alloys or metal compounds which are co- or sequentially deposited with the first metal or metals to be released. Alternatively, the different atoms or molecules may be adsorbed or trapped from the working gas atmosphere during reactive vapor deposition.

In U.S. Pat. No. 6,238,686 Burrell et al claim a modified material comprising one or more metals in a form characterized by sufficient atomic disorder such that the material, in contact with a solvent for the material, releases atoms, ions, molecules or clusters containing at least one metal at an enhanced rate relative to its normal ordered crystalline structure. In U.S. Pat. No. 5,681,575 Burrell et al claim a medical device which includes a coating of one or more anti-microbial metals having a "sufficient atomic disorder".

It is unclear from either U.S. Pat. No. 5,681,575 or U.S. Pat. No. 6,238,686 what would constitute a material characterized by "sufficient atomic disorder". In nature, most materials would exhibit sufficient atomic disorder if the true atomic disorder described (by drawings or mapping) in ordinary Chemistry or Physics handbooks were insufficiently ordered (with a regular geometric structure or like).

In any event, the teachings of Burrell et al appear to connect "atomic disorder" with an "enhanced rate" of release of "atoms, ions, molecules or clusters". If the term "release" further relates to a dissolution (as defined in textbooks of General Chemistry and Physics), then this dissolution should lead to the liberation of ions or molecules in solvent. When released in the solvent, these ions or molecules are usually solvated i.e. surrounded by the molecules of the solvent. It is very unlikely that atoms of a metal will be released into a solution comprising of water such as in the wound environment. If released into solution in its elemental state, metals would rather represent a relatively larger particles comprising of more than one or a few atoms.

As a result, the term "atom" as used in Burrell et al is not exactly descriptive. It is not known yet scientifically whether atoms of metals can be released into aqueous solutions at pH close to neutral (e.g., pH range 6 to 8), except in the case of colloidal solutions which are usually prepared by adequate chemical reactions in-situ.

U.S. Pat. No. 6,087,549 (Flick) discloses a multilayer laminate wound dressing comprising a plurality of layers of a fibrous material, with each layer comprising a unique ratio of metalized fibers to nonmetalized fibers. In a preferred embodiment the wound dressing consists of three layers and the metal is silver. The wound contact layer has the highest ratio of metalized fibers to nonmetalized fibers, the intermediate layer has a lower ratio of metalized fibers to nonmetalized fibers, and the outer layer has the lowest ratio of metalized fibers to nonmetalized fibers. The wound dressing described by Flick is commercially available under the trademark Silverlon™.

U.S. Pat. No. 5,211,855 (Antelman), U.S. Pat. No. 5,676,977 (Antelman) and U.S. Pat. No. 6,436,420 (Antelman) teach that tetrasilver tetroxide ($Ag_4O_4$) containing two monovalent and two trivalent silver ions exhibits bactericidal, fungicidal and algicidal properties. As a result, "tetrasilver tetroxide" is suggested for use for water treatment in U.S. Pat. No. 5,211,855 and for use in destroying the AIDS virus in U.S. Pat. No. 5,676,977.

In U.S. Pat. No. 6,436,420, Antelman describes a method of deposition or interstitial precipitation of tetrasilver tetroxide ($Ag_4O_4$) crystals within the interstices of fibers, yarns and/or fabrics forming such articles in order to produce fibrous textile articles possessing enhanced antimicrobial properties. The interstitial precipitation of $Ag_4O_4$ is achieved by immersion of the article to be treated (e.g., fiber, yarn or fabric) in an aqueous solution containing a water soluble silver salt, most preferably silver nitrate. After uniformly wetting the article, the article is removed into a second heated aqueous solution (having a temperature of at least 85 degrees Celsius or more preferably at least 90 degrees Celsius) containing strong alkali (most preferably NaOH) and a water soluble oxidizing agent (most preferably potassium persulfate) for 30 seconds to 5 minutes to facilitate the precipitation of tetrasilver tetroxide.

After the reaction is completed, the article is removed and washed. The article treated in this way is described as exhibiting outstanding antimicrobial resistance towards pathogens such as bacteria, viruses, yeast and algae. The article is also described as being resistant to ultraviolet light and as maintaining its antimicrobial properties after a number of launderings.

SUMMARY OF INVENTION

The present invention is directed at deposition products, composite materials and at methods for the production of deposition products and composite materials. The deposition products are comprised of at least one oxidized species of a metal.

The methods of the invention are based upon chemical deposition principles and techniques. The methods of the invention may be carried out under either acidic or alkaline conditions. The methods of the invention may comprise the step of exposing ions of the metal to an oxidizing agent to produce the deposition product. The methods of the invention may involve the production of the deposition product itself or the production of a composite material which comprises a substrate and the deposition product.

The methods of the invention are particularly suited for producing a composite material which is comprised of a substrate and a very thin coating or deposition layer of the deposition product. This thin coating or layer may be in the order of one or several atoms in thickness, which facilitates the production of a composite material which has a relatively high surface area to volume ratio. The coating may also be deposited so that it does not completely cover the substrate, thus leaving portions of the surface of the substrate uncoated. Composite materials produced using the methods of the invention may be useful for a variety of applications, including but not limited to electronics, materials engineering and medical applications.

The methods of the invention may be carried out at relatively low temperatures. Preferably the methods of the invention are carried out at temperatures of no greater than about 60 degrees Celsius. More preferably the methods of the invention are carried out at room temperature (i.e., between about 10 degrees Celsius and about 25 degrees Celsius).

The metal and the oxidizing agent are selected so that they are compatible with the production of the desired deposition product. As a result, any suitable metal and any suitable oxidizing agent may be used in the invention. The metal may also be comprised of more than one element, with the result that the deposition product may be comprised of at least one oxidized species of more than one metal element.

Preferably the metal is comprised of silver and the deposition product is comprised of at least one oxidized species comprising silver. The metal may, however, be further comprised of other metal elements such as gold, copper, tin or zinc so that the deposition product is comprised of at least one oxidized species comprising silver and one or more other metals.

Where the metal is comprised of silver, the resulting deposition product may exhibit significant antimicrobial properties. Without intending to be limited by theory, it is believed that these antimicrobial properties are due to the presence in the deposition product of one or more oxidized silver species. The presence of other metals in the deposition product may enhance these antimicrobial properties or may provide other complementary properties to the deposition product.

More particularly, it is believed that silver containing deposition products produced using the methods of the invention may be comprised of silver ions having valent states higher than one, such as for example Ag (II) and Ag (III) valent states. It is also believed that silver containing deposition products produced using the methods of the invention may be comprised of silver ions having more than one valent state so that the oxidized silver species may be comprised of a multivalent substance. Finally, it is believed that silver containing deposition products produced using the methods of the invention may be comprised of a silver containing substance or a plurality of silver containing substances which react over time to form other silver containing substances which may exhibit differing antimicrobial properties. It is believed that if this is the case, the deposition products produced by the invention may be useful for providing a varied antimicrobial response and for overcoming bacterial resistance.

In particular, in certain aspects, the methods of the invention may be used to produce a deposition product which comprises a substance having the general formula $Ag_7O_8X$, where X is an anion. The deposition product may be further comprised of $Ag_2SO_4$. The deposition product may also be comprised of other oxidized silver compounds such as one or more silver oxides selected from the group of silver oxides consisting of monovalent silver oxide, bivalent silver oxide, trivalent silver oxide and mixtures thereof.

The anion X may be comprised of a single anion or may be comprised of a plurality of different anions. The anion may therefore be comprised of any anion or combination of ions. The anion may, for example, be selected from the group of anions consisting of $HCO_3^-$, $CO_3^{2-}$, $NO_3^-$, $ClO_4^-$, $SO_4^{2-}$, $F^-$, and mixtures thereof. The source of the anion may be a metal compound which provides the ions of the metal. For example, where the deposition solution is comprised of a silver salt such as silver nitrate, the anion may be comprised of the nitrate ion ($NO_3^-$). An alternative or secondary source of the anion X may optionally be provided in order to provide sufficient quantities of the anion for production of the deposition product. Where an alternative or secondary source of the anion X is provided, the source of anions may be comprised of any source, including but not limited to any organic or inorganic acid.

Where the metal is comprised of silver, the composite materials produced by the methods may therefore be useful as medical devices or as components of medical devices due to their specific antimicrobial properties. These composite materials may also provide other advantages. As one example, the ability to provide a very thin coating or layer of the deposition product on the substrate makes it possible to minimize the amount of silver which must be used in the composite material in order to provide a desired antimicrobial response. As a second example, the ability to provide a very thin coating or layer of the deposition product on the substrate minimizes the extent to which the deposition product will interfere with the properties and functions of the substrate, particularly if the deposition product is deposited on the substrate so that it does not completely cover the surface of the substrate. This second example may be particularly significant where the substrate is comprised of an adhesive material such as a skin adhesive layer.

In a first aspect, the invention is a method for producing a composite material comprising a substrate and a deposition product, wherein the deposition product is comprised of at least one oxidized species of a metal, the method comprising the following steps:

(a) first contacting the substrate with a first basic environment comprising ions of the metal in order to expose the substrate to the ions of the metal; and (b) second contacting the substrate with a second basic environment in order to produce the composite material.

The first basic environment may be comprised of any environment in which metal ions are present under alkali conditions. The metal may be comprised of any metal or combinations of metals but preferably the metal is comprised of silver.

Preferably the first basic environment is comprised of a first basic solution comprising an amount of a silver diamino complex. More preferably, the first basic solution results from a mixture of a silver compound and ammonium hydroxide in an aqueous medium. Preferably the silver compound is selected from the group of silver compounds consisting of silver salts, silver oxides and mixtures thereof. More preferably the silver compound is comprised of silver nitrate.

The first basic solution may have any alkaline pH. Preferably the first basic solution has a pH in the range from about 8 to about 14. Within these parameters, the amount of ammonium hydroxide in the first basic solution is preferably selected such that a concentration of ammonium hydroxide in the first basic solution is between about 25 percent and about 35 percent by volume of the first basic solution. Preferably the amount of silver compound in the first basic solution is selected such that a concentration of the silver compound in the first basic solution is between about 1 gram per liter and about 20 grams per liter.

The second basic environment may be comprised of any environment having alkali conditions. Preferably the second basic environment is a strongly alkaline environment having a pH at least about 12. Preferably the second basic environment is comprised of a second basic solution containing an amount of a strong alkali compound. The strong alkali compound may be comprised of any compound which can provide the strong alkaline environment. For example, the strong alkali compound may be comprised of one or more Group I elements, including lithium, sodium, potassium, rubidium, cesium and francium. Preferably the strong alkali compound is selected from the group of compounds consisting of sodium hydroxide and potassium hydroxide and mixtures thereof and more preferably the strong alkali compound is comprised of sodium hydroxide. Preferably the amount of hydroxide compound in the second basic solution is selected such that a concentration of the hydroxide compound in the second basic solution is between about 15 grams per liter and about 35 grams per liter.

The first contacting step may be performed for any length of time which is sufficient to expose the substrate to the ions of the metal. Preferably the substrate is substantially completely exposed to the ions of the metal. Preferably the first contacting step is performed for between about 1 minute and about 10 minutes.

The second contacting step may be performed for any length of time which is sufficient to cause the production of the deposition product. Preferably the second contacting step is performed for a sufficient time in order to maximize the yield of the deposition product. Preferably the second contacting step is performed for between about 1 minute and about 60 minutes.

The first contacting step may be performed at any temperature. The second contacting step may be performed at any temperature. Preferably, however, the second contacting step is performed at a temperature of between about 2 degrees Celsius and about 60 degrees Celsius.

The method according to the first aspect may be further comprised of the step of washing the composite material following the second contacting step.

The method according to the first aspect may be further comprised of the step of adding an amount of an oxidizing agent to the second basic environment during the second contacting step. The oxidizing agent may be comprised of any oxidizing agent which is compatible with the metal, but the oxidizing agent is preferably selected from the group of oxidizing agents consisting of persulfates, permanganates, peroxides and mixtures thereof. More preferably the oxidizing agent is comprised of a persulfate. The persulfate may be comprised of any persulfate but preferably the persulfate is selected from the group of persulfates consisting of potassium persulfate, sodium persulfate, ammonium persulfate and mixtures thereof. More preferably the persulfate is comprised of ammonium persulfate, potassium persulfate or mixtures thereof, and most preferably the persulfate is comprised of potassium persulfate.

The amount of the oxidizing agent is preferably selected to be compatible with the amount of the ions of the metal so that the deposition product can be produced as efficiently as possible. In other words, the amount of the oxidizing agent is preferably selected to be a stoichiometrically appropriate amount relative to the amount of the ions of the metal. Preferably the amount of persulfate oxidizing agent is selected such that a concentration of the persulfate in the second basic solution is between about 1 gram per liter and about 25 grams per liter.

The method according to the first aspect may be further comprised of the step, prior to the first contacting step, of etching the substrate by immersing the substrate in an etching solution in order to prepare the substrate for the deposition product. The etching step may involve either or both of a physical process or a chemical process. The etching step preferably prepares the substrate for the deposition product by increasing the roughness of the substrate surface and/or creating attraction sites for adsorption and/or deposition of the deposition product.

Any etching solution may be utilized which is suitable for a particular substrate. For example, where the substrate is comprised of an organic material or polymer such as polyethylene, the etching solution is preferably comprised of a mixture of an alcohol and an aqueous solution of a hydroxide compound. The hydroxide compound may be comprised of any hydroxide compound but is preferably selected from the group of hydroxide compounds consisting of sodium hydroxide, potassium hydroxide and mixtures thereof. More preferably the hydroxide compound is comprised of sodium hydroxide. The etching step may be performed for any length of time sufficient to prepare the substrate, but preferably the etching step is performed for less than about 20 minutes and preferably is performed for at least 5 minutes.

The method according to the first aspect may be further comprised of the step of adding a residual silver compound to the second basic environment during the second contacting step. The residual silver compound may be comprised of any suitable source of silver ions, but preferably the residual silver compound is comprised of silver nitrate. Preferably the amount of residual silver compound is selected such that a concentration of the residual silver compound in the second basic solution is between about 1 gram per liter and about 5 grams per liter.

The method according to the first aspect may be further comprised of the step of agitating the second basic environment during at least a portion of the second contacting step in order to enhance the production of the deposition product and the composite material.

In a second aspect, the invention is a method for producing a deposition product, wherein the deposition product is comprised of at least one oxidized species of a metal, the method comprising the following steps:
(a) providing a deposition solution comprising an amount of ions of the metal and an amount of an oxidizing agent; and
(b) producing the deposition product by facilitating a chemical reaction in the deposition solution between the ions of the metal and the oxidizing agent.

The metal may be comprised of any metal or combinations of metals but preferably the metal is comprised of silver so that the ions of the metal are comprised of silver ions. The deposition solution may be comprised of silver ions from any source or in any form but preferably the deposition solution is comprised of an aqueous solution of a silver salt. More preferably the silver salt is comprised of silver nitrate.

The ions of the metal may be present in any concentration. Preferably, where the ions of the metal are comprised of silver ions, the amount of the silver ions is selected so that a concentration of the silver salt in the deposition solution is between about 1 gram per liter and about 20 grams per liter.

The oxidizing agent may be comprised of any oxidizing agent which is compatible with the metal, but the oxidizing agent is preferably selected from the group of oxidizing agents consisting of persulfates, permanganates, peroxides and mixtures thereof. More preferably the oxidizing agent is comprised of a persulfate. The persulfate may be comprised of any persulfate but preferably the persulfate is selected from the group of persulfates consisting of potassium persulfate, sodium persulfate, ammonium persulfate and mixtures thereof. More preferably the persulfate is comprised of ammonium persulfate, potassium persulfate or mixtures thereof, and most preferably the persulfate is comprised of potassium persulfate.

The amount of the oxidizing agent is preferably selected to be compatible with the amount of the ions of the metal so that the deposition product can be produced as efficiently as possible. In other words, the amount of the oxidizing agent is preferably selected to be a stoichiometrically appropriate amount relative to the amount of the ions of the metal. For example, where the metal is comprised of silver nitrate the amount of silver nitrate is preferably selected such that a concentration of the silver nitrate in the deposition solution is between about 1 gram per liter and about 20 grams per liter, in which case the amount of the oxidizing agent is preferably selected so that a concentration of the oxidizing agent in the deposition solution is between about 1 gram per liter and about 50 grams per liter.

The method according to the second aspect may be used to produce a deposition product which comprises a substance having the general formula $Ag_7O_8X$, where X is an anion. The deposition product may be further comprised of $Ag_2SO_4$. The deposition product may also be comprised of other oxidized silver compounds such as one or more silver oxides selected from the group of silver oxides consisting of monovalent silver oxide, bivalent silver oxide, trivalent silver oxide and mixtures thereof.

The anion X may be comprised of a single anion or may be comprised of a plurality of different anions. The anion may therefore be comprised of any anion or combination of ions. The anion may, for example, be selected from the group of anions consisting of $HCO_3^-$, $CO_3^{2-}$, $NO_3^-$, $ClO_4^-$, $SO_4^{2-}$, $F^-$, and mixtures thereof. The source of the anion may be a metal compound which provides the ions of the metal. For example, where the deposition solution is comprised of a silver salt such as silver nitrate, the anion may be comprised of the nitrate ion ($NO_3^-$). An alternative or secondary source of the anion X may optionally be provided in order to provide sufficient quantities of the anion for production of the deposition product.

As a result, in the method according to the second aspect, the method may be further comprised of the step of adding a source of anions to the deposition solution. The source of anions may be comprised of one or more acids. The acid may be comprised of any organic or inorganic acid. For example, the acid may be selected from the group of acids consisting of carbonic acid, nitric acid, perchloric acid, sulfuric acid, acetic acid, fluoroboric acid, phosphoric acid, phosphorous acid, citric acid, acetylsalicylic acid and mixtures thereof. The amount of the source of anions which is added to the deposition solution preferably is an amount which is selected to be compatible with the amount of the ions of the metal. In other words, the amount of the source of anions is preferably selected to be a stoichiometrically appropriate amount relative to the amount of the ions of the metal.

The deposition product producing step is preferably performed at a relatively low temperature, since the deposition product may experience increasing solubility with increasing temperature. The deposition product producing step is preferably performed at a temperature of between about 2 degrees Celsius and about 60 degrees Celsius, more preferably at a temperature of between about 2 degrees Celsius and about 40 degrees Celsius, and even more preferably at a temperature of between about 10 degrees Celsius and about 25 degrees Celsius.

Preferably the deposition solution is agitated during at least a portion of the deposition product producing step in order to enhance the production of the deposition product.

The method according to the second aspect may be used to produce the deposition product as a product, or may be used to produce a composite material comprising a substrate and the deposition product. Where the method is used to produce a composite material, the method may be further comprised of the following steps:
(a) providing a substrate; and
(b) contacting the substrate with the deposition solution during the deposition product producing step, thereby producing a composite material comprising the substrate and the deposition product.

The substrate contacting step may be performed for any length of time which is sufficient to produce the composite material having a desired composition. The substrate contacting step is preferably performed for at least about 1 minute, more preferably for between about 1 minute and about 60 minutes, even more preferably for between about 1 minute and about 20 minutes, and even more preferably for between about 2 minutes and about 10 minutes.

The method in the second aspect may be further comprised of the step, following the substrate contacting step, of washing the composite material.

The method according to the second aspect may be further comprised of the step, prior to the substrate contacting step, of etching the substrate by immersing the substrate in an etching solution in order to prepare the substrate for the deposition product. The etching step may involve either or both of a physical process or a chemical process. The etching step preferably prepares the substrate for the deposition product by increasing the roughness of the substrate surface and/or creating attraction sites for adsorption and/or deposition of the deposition product.

Any etching solution may be utilized which is suitable for a particular substrate. For example, where the substrate is comprised of an organic material or polymer such as polyethylene, the etching solution is preferably comprised of a mixture of an alcohol and an aqueous solution of a hydroxide compound. The hydroxide compound may be comprised of any hydroxide compound but is preferably selected from the group of hydroxide compounds consisting of sodium hydroxide, potassium hydroxide and mixtures thereof. More preferably the hydroxide compound is comprised of sodium hydroxide. The etching step may be performed for any length of time sufficient to prepare the substrate, but preferably the etching step is performed for less than about 20 minutes and preferably is performed for at least 5 minutes. Where the etching step is performed, the method according to the second aspect preferably further comprises the step, following the etching step, of washing the substrate to remove residual alkali from the substrate.

The method according to the second aspect may be further comprised of the step, following the substrate contacting step, of immersing the composite material in boiling water. The immersing step may be useful for converting the deposition product into other oxidized silver species (such as silver oxides), thus potentially providing an opportunity further to "engineer" the composite material to provide desired properties of the deposition product. The immersing step may be performed for any length of time, but preferably the immersing step is performed for at least about 1 minute.

The composite material may be produced for many different applications including for electronics, materials engineering and medical purposes. The method according to the second aspect is particularly suited for the production of medical devices in circumstances where the metal is silver and the deposition product is comprised of an oxidized silver species having the general formula $Ag_7O_8X$ and optionally $Ag_2SO_4$ and/or optionally one or more silver oxide compounds, due to the antimicrobial properties exhibited by the deposition product and to the capability to control the extent of the deposition of the deposition product on the substrate.

The term "medical device" as used herein means any article which has a medical application where antimicrobial properties may be desirable, and includes all natural and synthetic materials and both fibrous and non-fibrous materials. For example, the materials may be comprised of a metal, plastic, paper, glass, ceramic, textile, rubber, polymer, composite material or any other material or combination of materials. Non-limiting examples of medical devices which are encompassed by the invention include wound dressings, splints, sutures, catheters, implants, tracheal tubes, orthopedic devices, drains, shunts, connectors, prosthetic devices, needles, medical instruments, laboratory, clinic and hospital equipment, furniture and furnishings, dental devices, as well as health care products such as personal hygiene products, sterile packaging, clothing, footwear etc.

Accordingly, the composite material may comprise a medical device or a component of a medical device and the term "medical device" as used herein extends to both medical devices and components of medical devices.

In a preferred embodiment, the substrate is comprised of a wound dressing. The wound dressing may be comprised of any material or combination of materials, including but not limited to metals, ceramics, glass, polymers, plastics, composite materials, natural materials, synthetic materials, synthetic textiles such as HDPE, rayon, nylon, polyacetates, polyacrylics and glass and natural textiles such as cellulose, wool, jute and cotton, whether in fibrous or non-fibrous form.

In a preferred embodiment of wound dressing, the wound dressing may be comprised of a polymer material such as high density polyethylene and may be further comprised of an adhesive material comprising a skin adhesive layer. The skin adhesive layer may be comprised of a cross-linked silicon gel material. The wound dressing and/or the cross-linked silicon gel material may for example be comprised of a product sold under the Mepitel™ trade-mark or the Safetac™ trade-mark, both of which trade-marks are owned by Mölnlycke Health Care AB of Sweden.

In one application, the deposition product may be selectively deposited on the skin adhesive layer and the production of the deposition product is preferably controlled so that the deposition product does not materially interfere with the adhesive properties of the skin adhesive layer, yet still provides an acceptable antimicrobial effect without significant undesirable toxic effects. This result may be achieved by depositing the deposition product on the skin adhesive layer such that the deposition product provides a desired antimicrobial effect but does not completely cover the surface of the skin adhesive layer. In this application, preferably the amount of the deposition product which is deposited on the substrate is such that the amount of total silver on the substrate is selected to be between about 0.1 $mg/cm^2$ and about 1.0 $mg/cm^2$, or more preferably between about 0.2 $mg/cm^2$ and about 0.6 $mg/cm^2$, in order to achieve the desired result.

In other applications in which the deposition product is not deposited on an adhesive such as the skin adhesive layer, the amount of the deposition product is preferably controlled to balance the desired antimicrobial effect, undesirable toxic effects, and economic considerations.

In a third aspect, the invention is a medical device comprising a composite material, wherein the composite material is comprised of a substrate and a deposition product and wherein the deposition product is comprised of an antimicrobially active oxidized silver species comprising a silver salt and a silver oxide.

The medical device according to the third aspect may be produced using any of the methods of the invention. Preferably the medical device is produced using a method according to the second aspect of the invention.

In certain preferred embodiments the invention provides methods for depositing a deposition product comprising at least one oxidized silver species onto a substrate, thus producing a composite material. Since the oxidized silver species of the invention exhibit an antimicrobial activity, composite materials comprising the oxidized silver species can be used in various medical devices for prevention or inhibition of infections. These medical devices may include but are not limited to wound dressings, adhesives, sutures, catheters and other articles where antimicrobial properties are desirable.

The preferred embodiments of the invention may be used to produce deposition products and composite materials from aqueous solutions under a wide range of pH conditions, involving reactions in either acidic or alkaline solutions. The methods can be performed at, but are not limited to, temperatures between about 2 degrees Celsius and about 60 degrees Celsius with about 10 degrees Celsius to about 40 degrees Celsius being the most preferable.

The method steps for certain preferred embodiments of the invention are as follows:

I. Under Acidic Conditions:
   (a) immersing an article to be used as a medical device in an aqueous/alcohol solution of NaOH for a sufficient time to provide a reasonable etching and cleaning of the surface, followed by washing of the article with distilled water until a pH of 7 is attained, in order to remove residual alkali;

(b) immersing the article in an aqueous silver salt solution. The aqueous silver salt solution may be prepared from any silver salt which is soluble in water with the most preferred silver salt being silver nitrate;

(c) adding a stoichiometrically suitable quantity of an oxidizing agent to the mixed silver salt solution containing the article. The oxidizing agent can be any oxidizing substance such as persulfates, permanganates, hydrogen peroxide and the like, with potassium persulfate ($K_2S_2O_8$) being the most preferred oxidizing agent;

(d) adding a stoichiometrically suitable quantity of an acid to the mixed silver salt solution containing the immersed article in order to provide a source of anions. The acids that can be used include any inorganic or organic acids including, but not limited to carbonic acid, nitric acid, perchloric acid, sulfuric acid, acetic acid, fluoroboric acid, phosphoric acid, phosphorous acid, citric acid, acetylsalicylic acid and mixtures thereof, but most preferably nitric acid, perchloric acid, phosphoric acid, acetic acid or sulfuric acid;

(e) agitating the article in the mixed silver salt solution comprising the soluble silver salt (preferably $AgNO_3$), the acid (preferably nitric acid, perchloric acid, phosphoric acid, acetic acid or sulfuric acid), and the oxidizing agent (preferably potassium persulfate) at temperatures between 2 degrees Celsius and 30 degrees Celsius with temperatures between 10 degrees Celsius and 25 degrees Celsius being the most preferred for between about 2 and 40 minutes until the article is coated with a grayish, gray or black color;

(f) removing the article from the slurry and washing the article with distilled water until a pH of 7 is achieved; and (g) drying the article at room temperature.

Alternatively after step (e) the article may be immersed in boiling water (about 90 degrees Celsius to about 100 degrees Celsius) for at least 1 minute.

II. Under Alkaline Conditions:

(a) immersing an article to be used as a medical device in an aqueous/alcohol solution of NaOH for a sufficient time to provide a reasonable etching and cleaning of the surface;

(b) removing the article into a solution containing a silver diamino complex in a concentration sufficient to adsorb the silver ions at the surface of the article and for a duration of about 2 minutes to about 5 minutes. The silver diamino complex may be prepared by dissolving any silver salt or silver oxide in ammonium hydroxide, and may be achieved by adding a stoichiometrically suitable quantity of ammonium hydroxide to an aqueous solution or suspension of the silver salt or silver oxide until a clear colorless solution containing $[Ag(NH_3)_2]^+$ is obtained. The pH of this solution is usually in the range from about 8 to about 12;

(c) removing the article without washing or rinsing into another solution containing a strong alkali, most preferably NaOH or KOH, and agitating the article in this solution until a clear colorless solution is obtained and the article is clearly dyed with a tan, gray, brown or black color, depending on the desired amount of oxidized silver species. The time of contact of the article with the alkaline solution may vary, depending on temperature and silver ion concentration, but the most preferable duration is about 1 minute to about 15 minutes at room temperature or about 1 minute to about 10 minutes at a temperature of between about 40 degrees Celsius and about 60 degrees Celsius;

(d) removing the dyed article from the solution and washing with distilled water until a pH of 7 is achieved; and (e) drying the article at room temperature.

Alternatively, in step (c), the method may involve, depending on the amount of silver required at the surface of the article, further additions to the strong alkali solution of the silver diamino complex solution and/or additions to the strong alkali solution of an oxidizing agent such as a persulfate, permanganate, peroxide or a mixture thereof, with potassium persulfate being the most preferred oxidizing agent.

BRIEF DESCRIPTION OF DRAWINGS

Embodiments of the invention will now be described with reference to the accompanying drawings, in which:

FIG. 6(a) is a photograph depicting a controlled zone of inhibition (CZOI) against *Staphylococcus aureus* for a sample of HDPE mesh coated with a deposition product according to Examples 15-16.

FIG. 6(b) is a photograph depicting a controlled zone of inhibition (CZOI) against *Pseudomonas aeruginosa* for a sample of HDPE mesh coated with a deposition product according to Examples 15-16.

FIG. 6(c) is a photograph depicting a controlled zone of inhibition (CZOI) against *Candida albicans* for a sample of HDPE mesh coated with a deposition product according to Examples 15-16.

DETAILED DESCRIPTION

Figure 1:
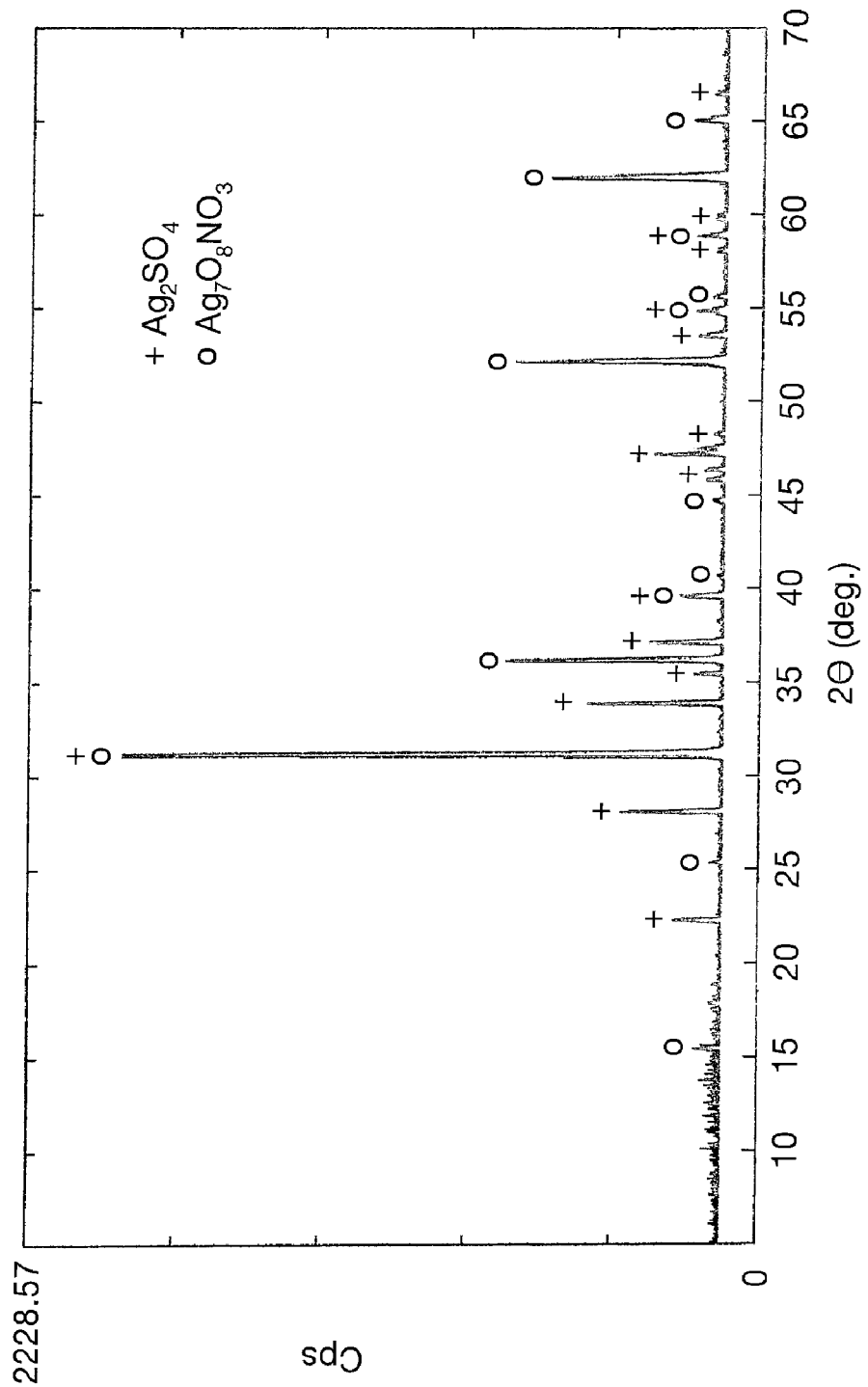
FIG. 1 is an XRD pattern generated from a deposition product obtained from the reaction of $AgNO_3$ and $(NH_4)_2S_2O_8$ according to Examples 15-16.

In preferred embodiments of the invention, antimicrobial properties of medical devices are achieved by the adsorption and deposition of a deposition product comprising an antimicrobially active silver species within or at the surface of the medical device. These active silver species may include but are not limited at all oxidized silver species such as silver salts, silver oxide ($Ag_2O$), higher silver oxides i.e. Ag(II) and Ag(III) ($AgO$, $Ag_2O_3$, $Ag_3O_4$ or like), silver oxy-salts with a general formula $Ag_7O_8X$ where X can include one of acid anions such as sulfates, chlorides, phosphates, carbonates, citrates, tartrates, oxalates and like. The deposition product may also contain some elemental silver deposited during the process.

The term "total silver" as used in herein is the total amount of silver as determined by a chemical analysis, which may include elemental (metallic) silver as well as silver originating from oxidized silver species.

The term "oxidized silver species" as used herein may involve but is not limited at all compounds of silver where said silver is in +I, +II or +III valent states or any combinations thereof. These oxidized silver species include, for example silver (I) oxide, silver (II) oxide, silver (III) oxide or mixtures thereof, all silver salts having a solubility product higher than $10^{-20}$ (such as for example $Ag_2SO_4$, $AgCl$, $Ag_2S_2O_8$, $Ag_2SO_3$, $Ag_2S_2O_3$, $Ag_3PO_4$, and the like), and silver oxy-salts such as $Ag_7O_8X$ were X can include but is not limited at $NO_3^-$, $ClO_4^-$, $SO_4^{2-}$, $F^-$ etc.

The term "medical device materials" as used herein may include materials such as metals, ceramics, glass, polymers, plastics, composite materials, a variety of natural materials, fabrics, textile made of either synthetic (HDPE, rayon, nylon, polyacetates, polyacrylics, glass etc.) or natural (cellulose, wool, jute, cotton, etc.) fibers.

The term "bacteriostatic activity", as used herein relates to the inhibition of bacterial growth, but not to actually killing the bacteria. Successful treatment therefore requires the host's immune system to clear the pathogen. Treatment is compromised when the antimicrobial materials are stopped before the pathogen has been completely cleared.

The term "bactericidal activity" as used herein relates to killing bacteria with or without lysis of the target cell. These types of antimicrobial materials are particularly advantageous in immunosuppressed individuals. A disadvantage to bactericidal activity is cell lysis, which can release lipolysaccharides which are toxic to the host. However, if the concentration of the said antimicrobial material is relatively low so that toxic effects cannot occur, a combination of both bacteriostatic and bactericidal activities may be ideal for antimicrobial materials.

In the preferred embodiments, the deposition of the deposition product comprising the oxidized silver species is accomplished by first providing an aqueous solution of monovalent silver salt or a silver complex such as silver nitrate, perchlorate or silver diamino complex, with silver nitrate being the most preferable if the reaction is carried out under acidic conditions or at close to neutral conditions (i.e. at pH below 7), and with silver diamino complex, (i.e., $[Ag(NH_3)_2]^+$) being the most preferable if the reaction is carried out under alkaline conditions (i.e. at pH above 7).

Prior to the production of the composite material comprising the article as a substrate and the deposition product, the article is preferably immersed in an alkaline solution containing 50 vol. % ethanol and 50 vol. % of an aqueous solution containing 30 g/L NaOH. Other cleaning and etching solutions can be used depending upon the material from which the medical device is made, upon the toxicity of the said cleaning or etching solutions, and upon the possibility that some toxic substances may adsorb at the surface of the article. Of course any use of toxic or carcinogenic substances during the etching step should be avoided. If production of the deposition product is carried out under acidic conditions, the article is preferably washed with distilled water after the etching step until a pH of 7 is achieved in order to remove residual alkali remaining after the etching step.

When the reaction is carried out in the pH range below 7 (i.e., under acidic conditions), the clean pretreated article to be used as a medical device containing oxidized silver species at the surface of the same is simply immersed into an agitated 1% $AgNO_3$ aqueous solution as a deposition solution. After exposure of the said article to the deposition solution for a duration preferably of about 2 to about 10 minutes, a solution of an oxidizing agent is added. Alternatively, the oxidizing agent may be added to the deposition solution before the article is immersed into the deposition solution, but this may result in some production of the deposition product before the article is present in the deposition solution.

Although a wide range of oxidizing agents such as permanganates, persulfates, hydrogen peroxide, hypochlorites etc., may be used under specific conditions and with the proper concentrations, the preferred oxidizing agent is a persulfate, more preferably either ammonium persulfate or potassium persulfate., and most preferably potassium persulfate The persulfate facilitates the precipitation and deposition of the deposition product on or within the article.

The concentration of persulfate in the deposition solution may be in a range from about 1 gram per liter to about 250 gram per liter with the concentration of about 50 gram per liter being the most preferable. After agitation for about 2 minutes to about 5 minutes, the solution of 1% $AgNO_3$ and persulfate may be acidified with an organic or inorganic acid such as $HNO_3$, $HClO_4$, $H_2SO_4$ or $CH_3COOH$ such that the concentration of the free acid preferably is about 9% $HNO_3$, 9% $HClO_4$ acid, 5% $H_2SO_4$, or 5% $CH_3COOH$. Although other acids may be used the most preferable acids are $H_2SO_4$, $HClO_4$ or $HNO_3$.

The agitation of the deposition solution is not strictly required, but in order to achieve a more uniform distribution of the deposition product and an efficient reaction yield, the agitation of the solution is recommended. Agitation can be realized by many different ways such as for example mechanical stirring, magnetic stirring or ultrasonic agitation.

Following addition of the persulfate (preferably potassium persulfate) to the deposition solution of 1% $AgNO_3$ within the time of about 1 minute to about 10 minutes, and depending on the concentration of the persulfate as well as on the conditions of agitation, the formation first of a yellow brown color of the solution and then a black grayish precipitate will occur. This brown color of the solution is attributed to the oxidation of Ag(I) to Ag(II).

The black grayish deposit at the article or in the bulk solution is a consequence of the formation of silver oxy-salts such as $Ag_7O_8X$, were X is an anion, depending on the acid used in the method e.g. $HNO_3$ ($NO_3-$), $H_2SO_4$ ($SO_4^{2-}$), etc. The decomposition of the silver oxy-salts may be presented as:

$$Ag(Ag_3O_4)_2X = AgX + AgO \tag{1}$$

Persulfates are powerful oxidizing agents. They can therefore be reduced in aqueous solutions according to the following reactions:

$$S_2O_8^{2-} + 2e^- = 2SO_4^{2-}, \text{with } E^0 = 1.96 \text{ V} \tag{2}$$

$$S_2O_8^{2-} + 2H^+ + 2e^- = 2HSO_4^-, \text{ with } E^0 = 1.96 \text{ V} \tag{3}$$

and $$S_2O_8^{2-} + 2H_2O = 2H^+ + 2SO_4^{2-} + H_2O_2, \text{ with } \Delta G^0 = -36 \text{ kJ/mol} \tag{4}$$

A consequence of the reduction of persulfate is the oxidation of Ag(I) to Ag(II) and Ag(III), probably according to the following reactions:

$$Ag^+ = Ag^{2+} + e^-, \text{ with } E^0 = 1.98 \text{ V} \tag{5}$$

$$Ag^+ + H_2O = AgO^+ + 2H^+ + e^-, \text{ with } E^0 = 1.998 \text{ V} \tag{6}$$

$$Ag^{2+} + H_2O = AgO^+ + 2H^+ + e^-, \text{ with } E^0 = 2.06 \text{ V} \tag{7}$$

$$Ag^+ + H_2O = AgO + 2H^+ + e^-, \text{ with } E^0 = 1.772 \text{ V} \tag{8}$$

In this way the composite material comprising the article to be used as a medical device and the deposition product may include a combination of oxidized silver species i.e. Ag(I)- and Ag(II)-oxides as well as silver salts such as nitrates, persulfates, sulfates, phosphates, perchlorates and like, silver salts of a general formula $Ag_7O_8X$ and perhaps traces of pure elemental silver. After production of the composite material, the article is removed from the deposition solution and then preferably washed with distilled water until a pH of 7 is achieved. When the washing is completed, the medical device comprising the composite material may be dried at room temperature and packaged.

When the reaction is carried out in the pH range above 7 (i.e., under alkaline conditions) the article to be used as a medical device is first immersed in an etching solution comprising an alkaline solution containing alcohol. The most preferable solution according to this invention is either NaOH or KOH with concentrations 15 to 40 g/L. The alcohol used in this solution may be ethyl alcohol, methyl alcohol or mixtures therein in a concentration above 50 vol. %. The immersion of the article into the etching solution is carried out in order to etch and clean the surface of the article to provide a reasonable adhesion of the deposition product comprising an oxidized silver species which is deposited on or within the article thereafter. The immersion time of the article is preferably in the range of between about 5 minutes and about 20 minutes, with about 10 minutes being the most preferable.

After the exposure to the alkali/alcohol solution for about 10 minutes, the article is then removed without washing or rinsing into a first basic environment comprising a first basic solution containing silver diamino complex i.e. $[Ag(NH_3)_2]^+$ in a concentration sufficient to adsorb silver ions at the surface of the article and for a duration of about 2 minutes to about 5 minutes. The silver diamino complex is preferably prepared from a silver salt or silver oxide dissolved or suspended in water by a dissolution with $NH_4OH$ (28 vol. %).

Consequently, the first basic solution is prepared in a way such that a solution of any silver salt (such as for example $AgNO_3$ or $AgClO_4$) or any silver oxide (such as $Ag_2O$ or $Ag_2O_2$ or AgO) or any silver salt suspended in water (such as AgCl, $Ag_2CO_3$, $Ag_2SO_4$ or the like), the ammonium hydroxide is added in a stoichiometrically suitable concentration so that a clear colorless solution is obtained. The concentration of silver ion in this silver diamino complex solution, as calculated for $Ag^+$ ion can vary from 1 to 20 g/L with about 10 g/L being the most preferable. The pH of the first basic solution is usually between about 8 and about 12 with the most preferred pH being in the range of between about 10 and about 11.

After exposure of the article to the first basic solution for about 2 minutes to about 5 minutes, the article is removed without washing or rinsing into a second basic environment comprising a second basic solution containing a strong alkali, most preferably NaOH or KOH. The article is kept in this solution under agitation until a clear colorless solution is obtained and the article is dyed with a tan, gray, brown or black color, depending on the desired amount of oxidized species to be deposited at or within the surface of the article. The time of contact of the article with the second basic solution may vary depending on temperature and the silver ion concentration, but most preferable time is about 1 minute to about 15 minutes at room temperature or about 1 minute to about 10 minutes at a temperature of between about 40 degrees Celsius and about 60 degrees Celsius.

Alternatively, the method may involve an addition of an oxidizing agent to the second basic solution, preferably a persulfate, more preferably either ammonium persulfate or potassium persulfate, and most preferably potassium persulfate. The oxidizing agent may be added directly to the second basic solution containing the article. In addition, depending on the amount of silver desired to be deposited as the deposition product, addition of a residual silver compound such as the silver diamino complex $[Ag(NH_3)_2]^+$ may also be beneficial.

Upon immersion of the article, previously exposed to the first basic solution, into the second basic solution, the following reaction at the surface of the article may occur:

$$2Ag(NH_3)_2NO_3 + 2NaOH = Ag_2O + 4NH_3 + H_2O + 2NaNO_3 \tag{9}$$

In this way, at the surface of the article, $Ag_2O$ will deposit as the result of the reaction (9). The addition of an oxidizing agent such as ammonium persulfate (i.e., $(NH_4)_3S_2O_8$) to the second basic solution may result in the oxidation of silver ions and the reduction of $S_2O_8^{2-}$ ions pursuant to the following reactions:

$$Ag^+ = Ag^{2+} + e^-, \text{ with } E^0 = 1.96 \text{ V} \tag{10}$$

and $$S_2O_8^{2-} + 2e^- = 2SO_4^{2-}, \text{ with } E^0 = 1.96 \text{ V} \tag{11}$$

The reactions of $Ag(NH_3)_2^+$ ion with ammonium persulfate can be represented as follows:

$$Ag(NH_3)_2NO_3 + (NH_4)_2S_2O_8 = Ag_2S_2O_8 + 2NH_4NO_3 + 4NH_3 \quad (12)$$

$$Ag_2S_2O_8 + H_2O = 2AgO + 2H_2SO_4 \quad (13)$$

$$Ag(NH_3)_2NO_3 + (NH_4)_2S_2O_8 + 2H_2O = 2NH_4NO_3 + 2AgO + 2H_2SO_4 + 4NH_3 \quad (14)$$

or $$Ag(NH_3)_2NO_3 + (NH_4)_2S_2O_8 + 2H_2O = 2NH_4NO_3 + 2AgO + 2(NH_4)_2SO_4 \quad (15)$$

In this way, the deposition product may contain $Ag_2O$, $AgO$ or other higher oxides of silver Ag(II), Ag(III) and mixtures therein. Also, if alcohol is present in the reacting solution, due to transferring from the etching solution some elemental silver may occur in the deposition product. This is because in the presence of persulfates, alcohols can be oxidized to aldehydes according to the reactions:

$$CH_3OH = H_2CO + 2H^+ + 2e^- \quad (16)$$

$$C_2H_5OH = CH_3CHO + 2H^+ + 2e^- \quad (17)$$

Under the alkaline conditions, the aldehydes can reduce the silver ions to the elemental silver according to the reaction:

$$2Ag(NH_3)_2OH + HCHO = 2Ag + 4NH_3 + HCOOH + H_2O \quad (18)$$

After production of the composite material comprising the article and the deposition product comprising the oxidized silver species is completed, the article is removed, carefully washed with water until a pH of 7 is achieved. The article may then be dried at room temperature and packaged.

Following are examples which illustrate the present invention.

EXAMPLES

Example 1

Nine (9) pieces of high density polyethylene mesh (HDPE), with dimensions 10 ×8 cm each, were immersed in 100 ml of an etching solution containing 50 mL alcohol (95% $C_2H_5OH$ and 5% $CH_3OH$) and 50 mL of 28 g/L NaOH solution for 5 minutes. After 5 minutes of etching the HDPE mesh was transferred without washing or rinsing into 40 mL of an $Ag^+$ solution, containing 15.3 g/L $AgNO_3$ and a stoichiometrically suitable volume of $NH_4OH$ (28 vol. %). The HDPE mesh was kept in this solution for 2 minutes. After 2 minutes of exposure to the ammoniacal $Ag(NH_3)_2^+$ solution, the HDPE mesh was transferred without washing or rinsing into 150 mL of a 28 g/L NaOH solution stirred with a magnetic stirrer. As soon as the HDPE mesh was immersed into NaOH solution, the formation of a precipitate yellowish-brown in color occurred. Under agitation a residual silver compound (about 38 mL of the Ag(I) solution) was added and after that 5 mL of a 250 g/L $(NH_4)_2S_2O_8$ solution was added. Agitation was continued for 10 minutes. During this time the solution/precipitate became black. The HDPE mesh was uniformly coated and was black and shiny in appearance. The coated HDPE mesh was then removed from the solution and carefully washed with distilled water until pH 7.00, and dried at room temperature. After drying, the mesh was a black and shiny in appearance.

Chemical analysis determined that the HDPE mesh coated with oxidized silver species contained about 0.08 mg total silver per cm² of mesh. The coated mesh was further analyzed by XRD analysis. As found by the XRD analysis the mesh included $Ag_2O$, Ag(II) oxides, $Ag_7O_8NO_3$ and some traces of the elemental silver. Both bacteriostatic and bactericidal activities of silver coated HDPE substrates were tested against *Pseudomonas aeruginosa* and *Staphylococcus aureus*. One hour bactericidal activity tests of coated HDPE mesh against both *Pseudomonas aeruginosa* and *Staphylococcus aureus* were positive. The bacteriostatic activity was also tested. The controlled zone of inhibition surrounding the test sample, where no bacteria growth occurred, was estimated at about 9 mm to about 10 mm.

Example 2

Samples of HDPE mesh with dimensions 10×8 cm were immersed in 100 mL of an etching solution containing 50 mL of 28 g/L NaOH and 50 mL of denatured ethanol (95% $C_2H_5OH$ and 5% $CH_3OH$) for 5 minutes. After 5 minutes of etching the HDPE mesh was transferred without washing or rinsing into 40 mL of an ammoniacal Ag(I) solution containing 15.3 g/L $AgNO_3$ and a stoichiometrically suitable quantity of $NH_4OH$ (28 vol. %). The HDPE mesh was kept in this solution for 2 minutes. The HDPE mesh was then transferred without washing or rinsing into 150 mL of a solution containing 28 g/L NaOH. The NaOH solution immediately became brown. Upon addition of a residual silver compound (about 38 mL of the Ag(I) solution) the solution turned to a dark brown color and with a continued agitation for about 5 minutes the solution became black. When the agitation was stopped, the black precipitate occurred in the bulk solution as a result of its separation from the HDPE mesh material. After washing and rinsing with distilled water the mesh appeared to be light tan or at the most slightly gray as a consequence of the coating with silver compounds.

The amount of total silver deposited on the HDPE mesh as determined by chemical analysis was estimated at about 0.04 mg/cm². Antimicrobial activities (bactericidal and bacteriostatic) were tested against *Pseudomonas aeruginosa* and *Staphylococcus aureus*. One hour bactericidal activity of the coated HDPE mesh was positive. The bacteriostatic activity, as estimated according to the controlled zone of inhibition (CZOI) for the bacterial growth was also positive. The CZOI was estimated at about 4 mm.

Example 3

Samples of HDPE mesh were immersed in an etching solution containing 100 mL of 28 g/L NaOH solution for 5 minutes. The mesh was then transferred without washing or rinsing into 40 mL of an ammoniacal Ag(I) solution containing 15.3 g/L $AgNO_3$ and a stoichiometrically suitable volume of $NH_4OH$ (28%). After 2 minutes of immersion, the mesh was transferred without washing or rinsing into 150 mL of a 28 g/L NaOH solution stirred magnetically. The solution became immediately brown due to formation of a precipitate. Addition of a residual silver compound (about 38 mL of the Ag(I) solution) resulted in the formation of a dark brown precipitate. The color of the solution did not change further even after 30 minutes of mixing at room temperature. The HDPE mesh was then washed and rinsed very carefully with distilled water. The color of the HDPE mesh did not change significantly, but some change in color from white to a light tan appeared.

The amount of total silver deposited on the HDPE mesh was estimated at about 0.02 mg/cm$^2$. The antimicrobial activities (both bacteriostatic and bactericidal) of these samples were tested against *Pseudomonas aeruginosa* and *Staphylococcus aureus*. The results showed a positive bactericidal activity and the CZOI was estimated at about 3 mm.

Example 4

Samples of HDPE mesh were immersed in 100 mL of a solution containing 1 g AgNO$_3$ and 1 mL of 67% HNO$_3$ as a source of anions. After 5 minutes of immersion, 5 g of (NH$_4$)$_2$S$_2$O$_8$ dissolved in 20 mL of water was added. The sample was left for 30 minutes at room temperature, during which the solution was stirred occasionally with a glass rod. During this time the solution changed color from colorless to a dark brown and a formation of a light gray precipitate in the bulk solution appeared. After 30 minutes, the HDPE mesh was removed from the solution and carefully washed with distilled water. The washed HDPE mesh had a gray color. The coating was uniformly distributed at the surface of this material.

The amount of total silver deposited on the HDPE mesh was estimated at 0.09 mg/cm$^2$. The bactericidal activity for these samples was positive. The CZOI was estimated at about 8 mm.

Example 5

HDPE mesh was coated with silver oxidized compounds using a method similar to that described in Example 4, with a few differences as outlined in the description that follows.

Samples of HDPE mesh were immersed in 100 mL of a solution containing 10 g/L AgNO$_3$ and 15 mL/L HNO$_3$ (67%) as a source of anions. To this solution 10 mL of 500 g/L (NH$_4$)$_2$S$_2$O$_8$ was added. The solution was magnetically stirred. After 7 minutes of stirring the solution became yellow-brown and formation of a very small amount of precipitate occurred. The stirring was continued for the next 30 minutes. After 30 minutes, the HDPE mesh was removed from the slurry and carefully washed with distilled water. The washed HDPE mesh had a gray color. The coating was uniformly distributed at the surface of the HDPE mesh.

The amount of total silver deposited on the HDPE mesh was estimated at 0.08 mg/cm$^2$. The bactericidal activities against *Pseudomonas aeruginosa* and *Staphylococcus aureus* were positive. The CZOI was estimated at about 7 mm.

Example 6

HDPE mesh was coated with silver oxidized compounds using a method similar to that described in Example 4 and Example 5, with a few differences as outlined in the description that follows.

Samples of HDPE mesh were immersed in 100 mL of a solution containing 10 g/L AgNO$_3$ and 15 mL/L HNO$_3$ (67%) as a source of anions. To this solution 10 mL of 500 g/L (NH$_4$)$_2$S$_2$O$_8$ was added. The solution was agitated ultrasonically. After 2 minutes of stirring the solution became yellow-brown and formation of a very small amount of precipitate occurred. The stirring was continued for the next 30 minutes. After 30 minutes, the HDPE mesh was removed from the solution and carefully washed with distilled water. The washed HDPE mesh had a gray color. The coating was uniformly distributed at the surface of the HDPE mesh.

The amount of total silver deposited on the HDPE mesh was estimated at 0.08 mg/cm$^2$. The bactericidal activities against *Pseudomonas aeruginosa* and *Staphylococcus aureus* were positive. The CZOI was estimated at about 7 mm.

Examples 7-9

In these examples the effect of different acids (i.e., sources of anions) is clearly shown for coating of HDPE mesh with oxidized silver species under acidic conditions. In Example 4, HNO$_3$ was used as a source of anions to supplement the anions contained in the AgNO$_3$, while in Examples 7-9 perchloric acid (HClO$_4$), sulfuric acid (H$_2$SO$_4$) and acetic acid (CH$_3$COOH) respectively were used as a source of anions.

Samples of HDPE mesh were immersed in 100 mL of a solution containing 1 g AgNO$_3$. To this solution 1 mL of HClO$_4$ (70%) (Example 7), 0.5 mL of H$_2$SO$_4$ (98%) (Example 8) and 15 mL of CH$_3$COOH (5%) (Example 9) were added. After 2 minutes of the exposure of HDPE mesh to these solutions, 20 mL of 250 g/L (NH$_4$)$_2$S$_2$O$_8$ was added. The mixing was continued for the next 30 minutes. In the solutions containing HClO$_4$ (Example 7) and H$_2$SO$_4$ (Example 8) formation of a black grayish precipitate occurred similar to Example 4. When the precipitate settled the solutions were clear and yellow-brown in color. The yellow-brown color suggests the presence of Ag(II) complexes in the solution. The coated HDPE mesh was then removed from the slurry and carefully washed and rinsed with distilled water and thereafter dried at room temperature. After drying the HDPE mesh coated in the presence of 1 mL of HClO$_4$ (70%) (Example 7), or in the presence of 0.5 mL of H$_2$SO$_4$ (98%) (Example 8) appeared to be grayish in color. However, the HDPE mesh coated in the presence of 15 mL of CH$_3$COOH (5%) (Example 9) was white and it did not change its color.

The coated HDPE mesh (Examples 7-9) were analyzed for the total silver content, and the antimicrobial activity was also evaluated against *Pseudomonas aeruginosa* and *Staphylococcus aureus*. The amount of total silver deposited on the HDPE mesh was estimated at 0.08 mg/cm$^2$ (for samples coated in the presence of HClO$_4$), 0.07 mg/cm$^2$ (for samples coated in the presence of H$_2$SO$_4$) and 0.01 mg/cm$^2$ (for the samples coated in the presence of CH$_3$COOH). The bactericidal activities against *Pseudomonas aeruginosa* and *Staphylococcus aureus* were positive. The CZOI was estimated at about 6 mm (for samples coated in the presence of HClO$_4$ or H$_2$SO$_4$) and about 1 to 2 mm (for samples coated in the presence of CH3COOH).

Example 10

Samples of HDPE mesh with dimensions 10×8 cm were immersed in 100 mL of an etching solution containing 50 mL of 28 g/L NaOH and 50 mL of denatured ethanol (95% C$_2$H$_5$OH and 5% CH$_3$OH) for 5 minutes. After 5 minutes of etching the HDPE mesh was transferred without washing or rinsing into 40 mL of an ammoniacal Ag(I) solution containing 15.3 g/L AgNO$_3$ and a stoichiometrically suitable quantity of NH$_4$OH (28 vol. %). The HDPE mesh was kept in this solution for 2 minutes. The HDPE mesh was then transferred without washing or rinsing into 150 mL of a solution containing 28 g/L NaOH. The NaOH solution immediately became brown. After mixing for 2 minutes, the solution became clear and colorless and the mesh was tan in color. When the agitation was stopped, the HDPE mesh was removed from solution and washed with distilled water. After washing and rinsing the mesh appeared to be tan in color as a consequence of the coating with silver compounds.

The coated HDPE mesh was analyzed for silver content and for antimicrobial activity against *Pseudomonas aerugi*- nosa and *Staphylococcus aureus*. These samples contained between 0.04 and 0.08 mg/cm total silver. The bactericidal activities against *Pseudomonas aeruginosa* and *Staphylococcus aureus* were positive. The CZOI was estimated at about 10 mm.

Example 11

A patterned wound dressing made of a perforated plastic carrier material with a skin adhesive layer comprised of a hydrophobic cross-linked silicon gel (trade-mark Mepitel™, product of Mölnlycke Health Care AB, Sweden), dimensions 8×15 cm was exposed to a solution containing 15 g/L NaOH at room temperature for 5 minutes. Under conditions of agitation 40 mL of a solution containing 15.3 g/L $AgNO_3$ and a proper volume of $NH_4OH$ (28 vol. %) was added. The wound dressing was kept in this solution and agitated for the next 5 minutes. The wound dressing was then removed from the solution and carefully washed with distilled water. Drops of water were removed with a soft paper and the wound dressing was dried at room temperature.

The coated wound dressing was analyzed for antimicrobial activity against *Pseudomonas aeruginosa* and *Staphylococcus aureus*. MH plates and Tryptic Soy Broth were used for analysis. *Pseudomonas aeruginosa* standard was set to 0.5 McFarland standard. One hour of bactericidal activity of the coated wound dressing against the bacteria where TSB broths were incubated for 24 hours was positive. The controlled zones of inhibition (CZOI), for the bacterial growth (bacteriostatic activity) were above 8 mm. The same samples of coated wound dressing were tested for seven days for antimicrobial activity. The values of CZOI after 2 days were 20.5 mm, after 3 days 19 mm, after 4 days 20.5 mm, after 5 days 19 mm and after 7 days 7 mm. These results show very good resistance towards bacteria for a relatively long time (7 days).

Example 12

A patterned wound dressing made of a perforated plastic carrier material with a skin adhesive layer comprised of a hydrophobic cross-linked silicon gel (trade-mark Mepitel™, product of Mölnlycke Health Care AB, Sweden), dimensions 8×15 cm was exposed to 500 mL of a 1% $AgNO_3$ solution. To this solution was added 200 mL of a solution containing 20 g $K_2S_2O_8$ and mixing was continuous for the next 20 minutes. The wound dressing was then removed from the solution and carefully washed with distilled water. Drops of water were removed with soft paper and the wound dressing was dried at room temperature.

The coated wound dressing contained 0.25-0.55 mg/cm$^2$ of total silver. The coated wound dressing was then analyzed for antimicrobial activity in the same manner as described in Example 11. The results showed excellent antimicrobial activity for 7 days.

Example 13

A patterned wound dressing made of a perforated plastic carrier material with a skin adhesive layer comprised of a hydrophobic cross-linked silicon gel (trade-mark Mepitel™, product of Mölnlycke Health Care AB, Sweden), dimensions 8×15 cm was coated in a way as described in Example 12, except that $(NH_4)_2 S_2O_8$ was used as an oxidizing agent instead of $K_2S_2O_8$, in the same amount and in the same manner as described in Example 12.

The coated wound dressing produced as described in this example was analyzed for the antimicrobial activity. The results showed excellent antimicrobial activity.

Example 14

A slurry was prepared by mixing 500 mL of a 1% $AgNO_3$ solution and 200 mL of an aqueous solution containing 20 g $K_2S_2O_8$ for 10 minutes. To this slurry a patterned wound dressing made of a perforated plastic carrier material with a skin adhesive layer comprised of a hydrophobic cross-linked silicon gel (trade-mark Mepitel™, product of Mölnlycke Health Care AB, Sweden), dimensions of 8×15 cm was added and mixing was continued for the next 20 minutes. The coated wound dressing was then removed from the slurry, carefully washed with water then dried as described in the Example 12. The coated wound dressing was black-greyish in appearance.

The antimicrobial activity of the coated wound dressing was tested in a way described in Example 11. The results showed excellent antimicrobial activity for seven days.

Examples 15-16

All method steps were performed at room temperature (22 degrees Celsius±2 degrees Celsius), unless otherwise specified.

Samples of HDPE mesh were coated with oxidized silver species as follows. HDPE mesh with dimensions 10×10 cm were immersed into 100 mL of a 1% $AgNO_3$ solution and thoroughly wetted. After the exposure of the HDPE mesh to the solution for 10 minutes, 20 mL of a solution containing either 250 g/L of $(NH_4)_2S_2O_8$ or 250 g/L of $K_2S_2O_8$ was added under magnetic stirring. The mixing was continued for the next 15 minutes. The coated HDPE mesh was then removed from the slurry and was observed to be grayish-black in appearance. After coating, the HDPE mesh was washed with water and then dried.

The bacteriostatic activity for the controlled zone of inhibition (CZOI) of bacterial or fungal growth was tested against *Pseudomonas aeruginosa*, *Staphylococcus aureus* or *Candida albicans*, using standard procedures as described in the literature.

Discussion of Examples 15-16

(a) Deposition of Silver Deposition Products Using $(NH_4)_2 S_2O_8$

Upon addition of ammonium persulfate to the $AgNO_3$ solution, a gradual color change from colorless through yellow, brown and finally to a cloud solution containing grayish-black precipitate was observed. Time for the appearance of the grayish-black precipitate at room temperature was estimated at 5 to 10 minutes. It was noted that if the reaction takes place at temperatures above 30 degrees Celsius, the precipitation and color change do not occur.

Persulfates are powerful oxidizing agents. In aqueous solutions persulfates can be reduced to sulfates (S. I. Zhdanov, *Sulfur, Selenium, Tellurium and Polonium*, in *Standard Potentials in Aqueous Solutions*, A. J. Bard, R. Parsons and J. Jordan Editors, Marcel Dekker Inc., New York (1985)). A consequence of the reduction of persulfate is the oxidation of Ag(I) to Ag(II) and Ag(II) to Ag(III). The grayish-black precipitate deposited on the HDPE mesh was formed as a result of the reduction of persulfate and a consequent oxidation of Ag(I) ions.

During precipitation of the deposition product, the pH of the solution dropped from about 2 to below 1. The decrease in pH of the solution was more significant when $K_2S_2O_8$ is used as an oxidizing agent instead of $(NH_4)_2S_2O_8$, in that a decrease in pH from about 7 to below 1 was observed.

(b) Properties of Deposition Products Produced Using $(NH_4)_2S_2O_8$

The grayish-black precipitate itself represents a mixture of silver argentic nitrate $Ag(Ag_3O_4)_2NO_3 \leftrightarrow Ag_7NO_{11}$ and $Ag_2SO_4$. Indeed, as found by XRD analysis, the peaks in the patterns showed a reasonable match for $Ag_2SO_4$ and $Ag_7O_8NO_3$ (FIG. 1). It is apparent that the oxidation of $AgNO_3$ with $(NH_4)_2S_2O_8$ leads to the precipitation of silver oxy-salt $Ag_7NO_{11}$ and also $Ag_2SO_4$. The precipitation of $Ag_2SO_4$ is usually not observed when $K_2S_2O_8$ is used as an oxidizing agent of Ag(I) ions (see the discussion below relating to oxidation with $K_2S_2O_8$).

Figure 2:
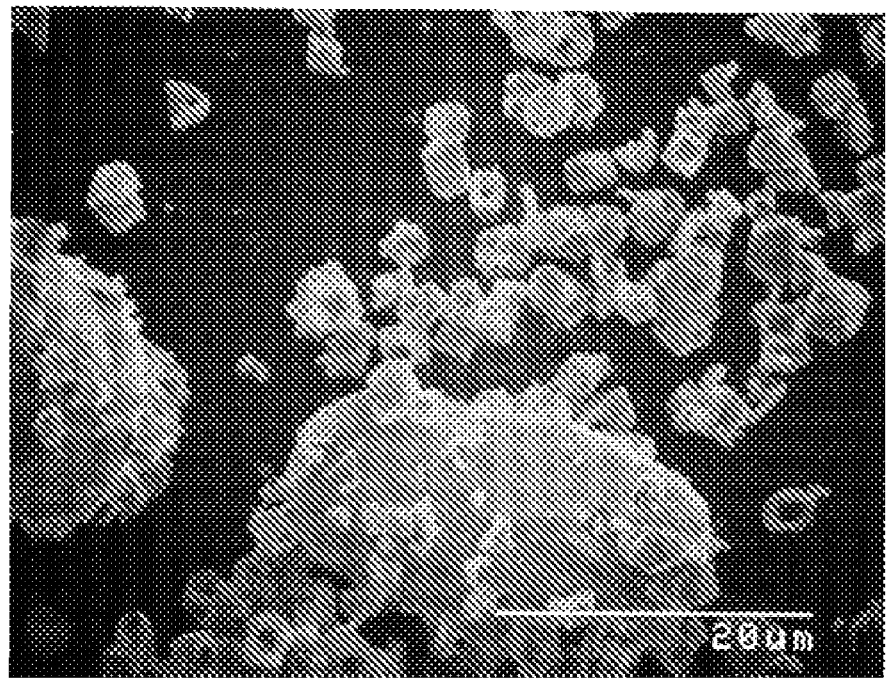
FIG. 2 is an SEM micrograph (magnification=2000×) generated from a deposition product obtained from the reaction of $AgNO_3$ and $(NH_4)_2S_2O_8$ according to Examples 15-16.

FIG. 2 provides a SEM micrograph of the grayish black precipitate. The smaller "cubical" particles represent $Ag_7O_8NO_3$ and their size, based on SEM is estimated at about 2.5 μm. The shape of these particles was found to be in very good agreement with the results of Skanavi-Grigoreva (M. S. Skanavi-Grigoreva, I. L. Shimanovich, *Zh. Obsh., Khim.*, 24, 1490(1954)). Who produced this material by the electrolysis of an aqueous $AgNO_3$ solution. The larger, cylindrical particles represent silver sulfate ($Ag_2SO_4$).

(c) Deposition of Silver Deposition Products Using $K_2S_2O_8$

Some differences in the formation of the grayish-black precipitate were observed when $K_2S_2O_8$ was used instead of $(NH_4)_2S_2O_8$, as the oxidizing agent of Ag(I). The precipitation of the grayish-black compound was significantly faster, and occurred within 1 minute upon addition of $K_2S_2O_8$ to the $AgNO_3$ solution. During this time, the pH of the solution changed from the initial pH of about 7 to below 1 after the precipitation.

(d) Properties of Deposition Products Produced Using $K_2S_2O_8$

Figure 3:
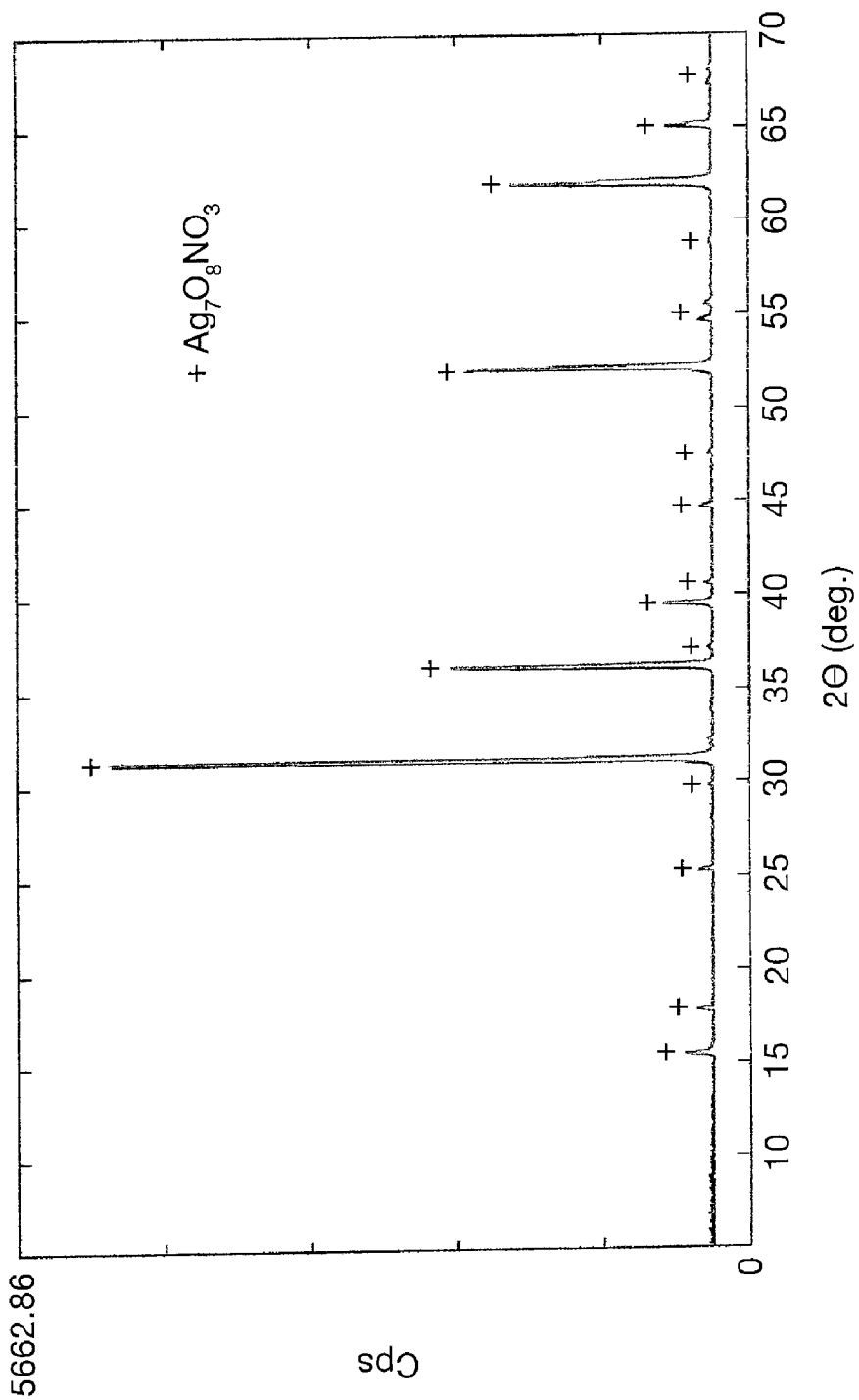
FIG. 3 is an XRD pattern generated from a deposition product obtained from the reaction of $AgNO_3$ and $K_2S_2O_8$ according to Examples 15-16.

As determined by XRD analysis in FIG. 3, all the peaks in the pattern exactly match the compound of composition $Ag_7O_8NO_3$. No other compounds were identified in this XRD pattern.

The theoretical amount of Ag in the compound $Ag_7O_8NO_3$ is 79.90%. The chemical analysis determined that the grayish black precipitate contained about 78.80% Ag. This result shows a good agreement of the experiments with the theory.

Figure 4:
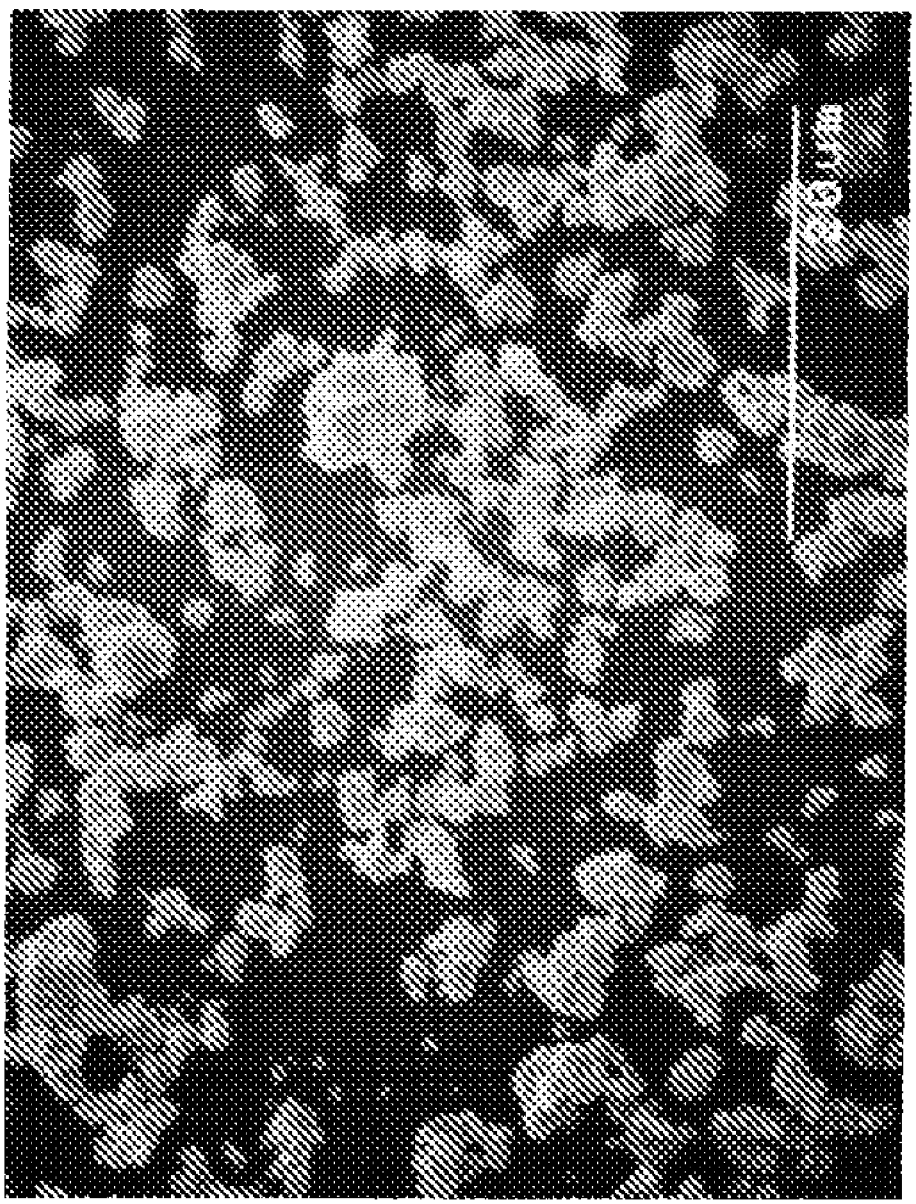
FIG. 4 is an SEM micrograph (magnification=2000×) generated from a deposition product obtained from the reaction of $AgNO_3$ and $K_2S_2O_8$ according to Examples 15-16.

The SEM micrographs of the powder produced by the chemical oxidation of $AgNO_3$ with $K_2S_2O_8$ are presented in FIG. 4. It appears that the particles are uniform and cubical in their shape. The size of these particles is estimated at about 2.5 μm.

(e) Antimicrobial Activity

Figure 5A:
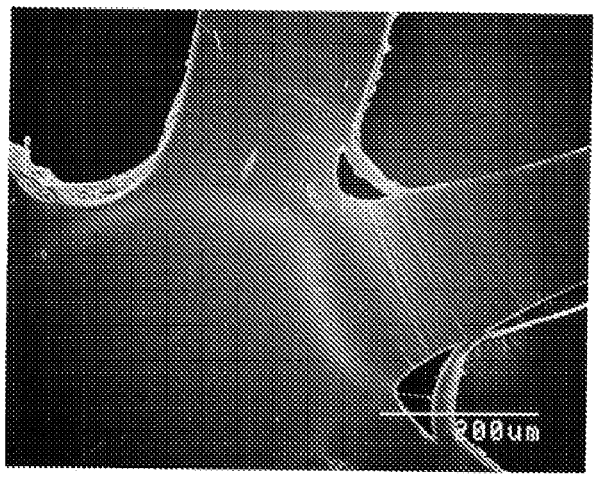
FIG. 5(a) is an SEM micrograph (magnification=150×) generated from a sample of uncoated HDPE mesh.
Figure 5B:
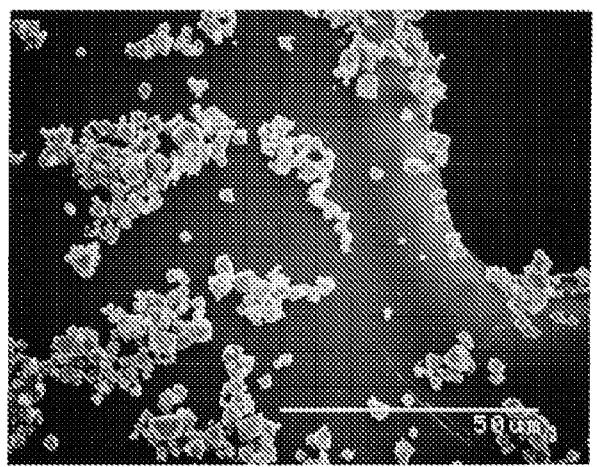
FIG. 5(b) is an SEM micrograph (magnification=1000×) generated from a sample of HDPE mesh upon which a deposition product has been deposited according to Examples 15-16.

The comparison of the SEM micrographs of uncoated and coated HDPE mesh samples is presented in FIG. 5. As shown in FIG. 5, the surface of the HDPE is partially covered with the $Ag(Ag_3O_4)_2NO_3$ particulates.

These samples were tested for bioactivity against the bacteria *Pseudomonas aeruginosa, Staphylococcus aureus* or fungi *Candida albicans*. As can be seen from the photographs presented in FIG. 6, clear zones surrounding the test samples (where a growth of tested microorganisms did not occur) were observed in all cases for *Staphylococcus aureus* (a gram-positive bacteria), *Pseudomonas aeuguginosa* (a gram-negative bacteria) and *Candida albicans* (an example of fungi). The size of the controlled zone of inhibition (CZOI), where the growth of tested microorganisms was not observed, was estimated at 3 mm to 5 mm for all tested samples. These results suggest that the deposition products have antibacterial and antifungal properties. Furthermore these results are in agreement with previously published results, where was suggested that only oxidized silver species, but not metallic silver exhibit an antimicrobial activity.

(f) Conclusions Relating to Examples 15-16

It has been demonstrated that deposition products, namely those of composition $Ag_7NO_{11} \times 3Ag_2SO_4$ or $Ag_7NO_{11}$ can successfully be deposited as powders or on a substrate such as HDPE mesh, by a simple reaction between $AgNO_3$ and $(NH_4)_2S_2O_8$ or $K_2S_2O_8$. These compounds are soluble in both concentrated $HNO_3$ or $NH_4OH$.

Example 17

Samples of a substrate consisting of a patterned wound dressing made of a perforated plastic carrier material with a skin adhesive layer comprised of a hydrophobic cross-linked silicon gel (trade-mark Mepitel™, product of Mölnlycke Health Care AB, Sweden) were subjected to SEM micrography to observe the density and coverage on the substrate of a deposition product deposited on the substrate in accordance with the second and third aspects of the invention, and to XRD analysis to analyze the composition of the deposition product deposited on the substrate.

Figure 7:
FIG. 7 is an SEM micrograph (magnification=30×) generated from a substrate consisting of an uncoated sample of a perforated plastic carrier material with a skin adhesive layer comprised of a hydrophobic cross-linked silicon gel (trade-mark Mepitel™).

FIG. 7 depicts an uncoated sample of the Mepitel™ wound dressing at a magnification of 30×. FIGS. 8-11 depict samples of composite materials which have been produced according to the second and third aspects of the invention in the same manner as described in Example 14.

Figure 8:
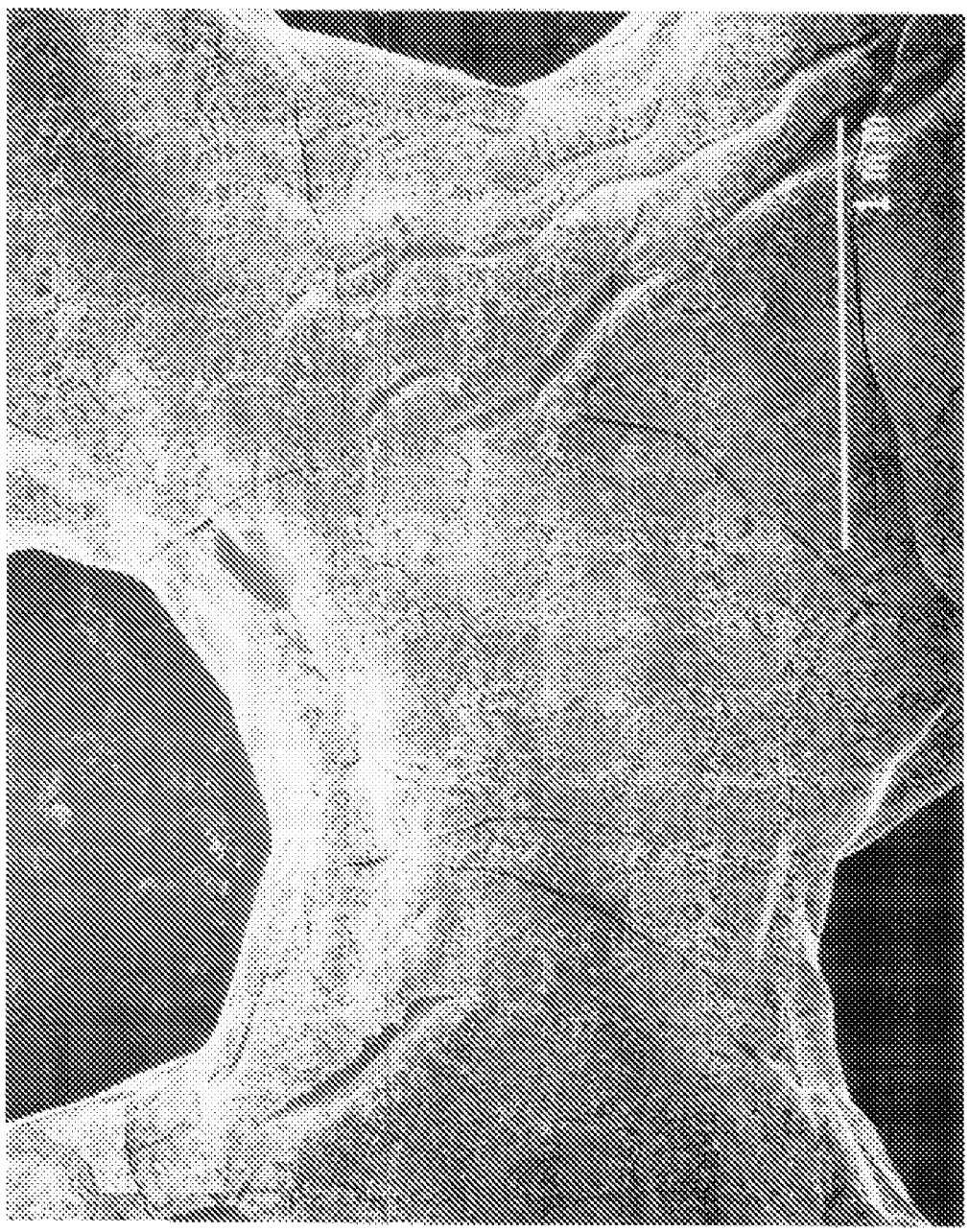
FIG. 8 is an SEM micrograph (magnification=40×) generated from a composite material consisting of a coated sample of a perforated plastic carrier material with a skin adhesive layer comprised of a hydrophobic cross-linked silicon gel (trade-mark Mepitel™), in which a relatively small amount of deposition product has been deposited on the substrate in accordance with the second and third aspects of the invention.
Figure 9:
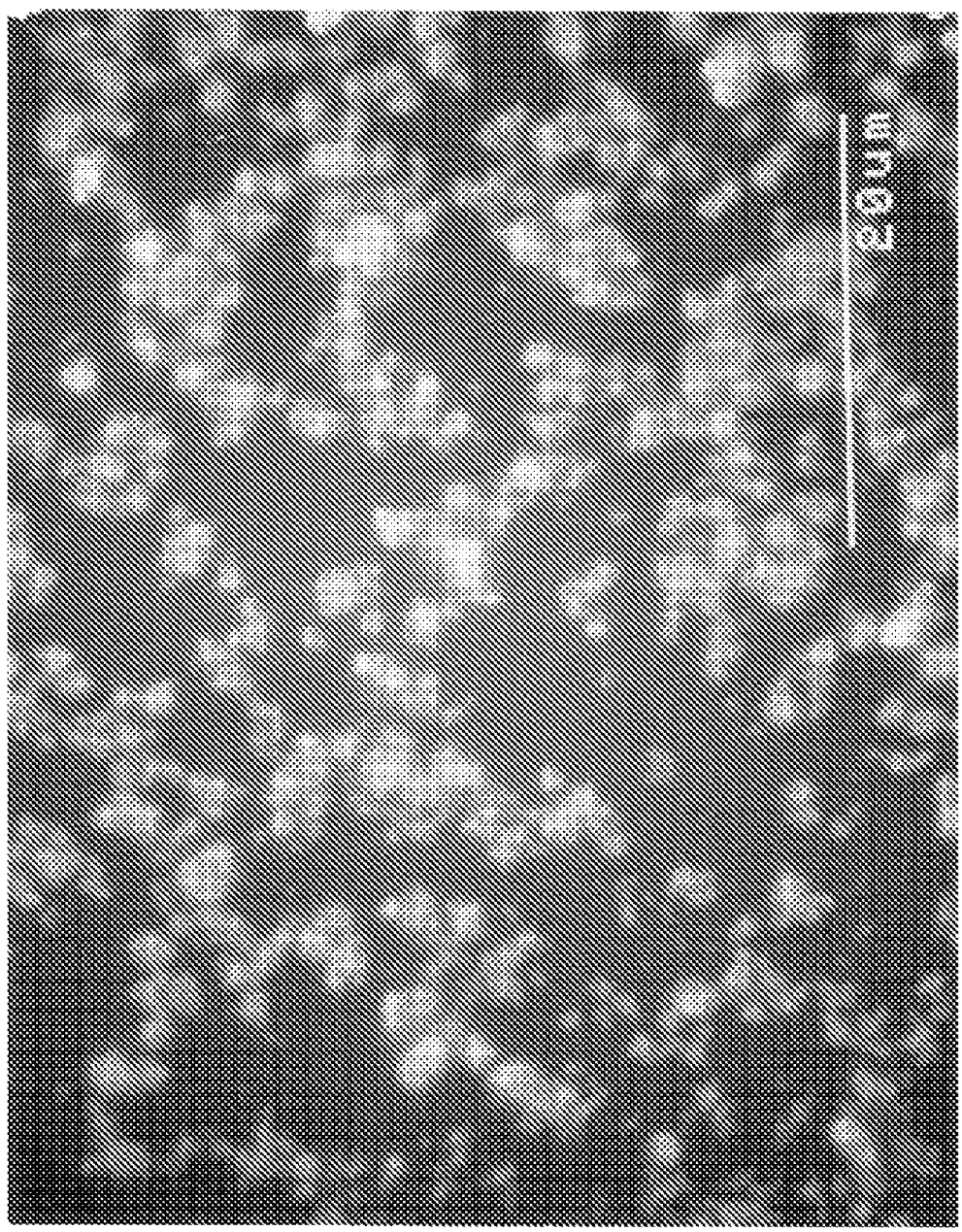
FIG. 9 is an SEM micrograph (magnification=2000×) generated from the composite material of FIG. 8, depicting the density and coverage of the deposition product on the substrate.

FIG. 8 depicts a composite material comprising a coated sample of the Mepitel™ wound dressing at a magnification of 40×, in which a relatively low amount of deposition product has been deposited on the substrate. FIG. 9 depicts the composite material of FIG. 8 at a magnification of 2000×, and clearly shows that the density and coverage of the deposition product is such that the skin adhesive layer of the Mepitel™ wound dressing is relatively unobstructed by the deposition product.

Figure 10:
FIG. 10 is an SEM micrograph (magnification=40×) generated from a composite material consisting of a coated sample of a perforated plastic carrier material with a skin adhesive layer comprised of a hydrophobic cross-linked silicon gel (trade-mark Mepitel™), in which a relatively larger amount of deposition product (relative to FIG. 8 and FIG. 9) has been deposited on the substrate in accordance with the second and third aspects of the invention.
Figure 11:
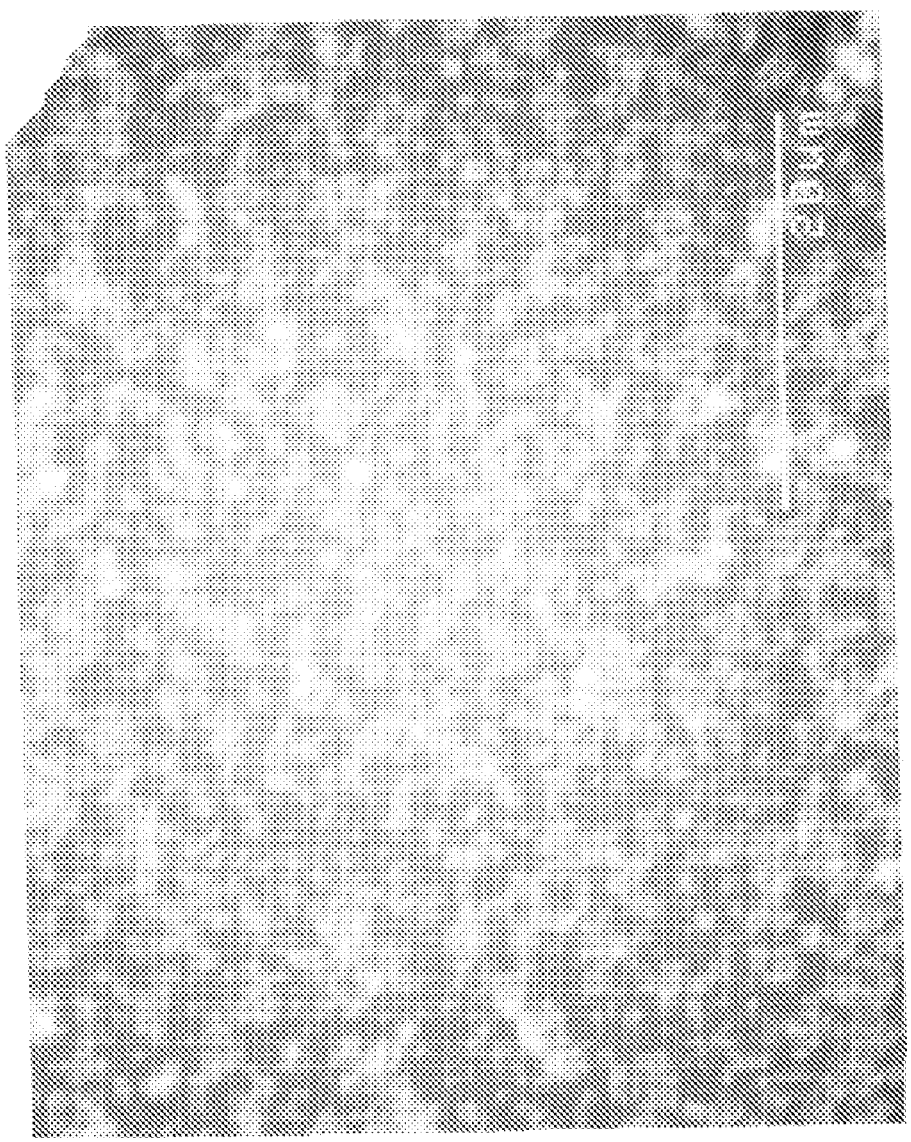
FIG. 11 is an SEM micrograph (magnification=2000×) generated from the composite material of FIG. 10, depicting the density and coverage of the deposition product on the substrate.

FIG. 10 depicts a composite material comprising a coated sample of the Mepitel™ wound dressing at a magnification of 40×, in which a higher amount of deposition product has been deposited on the substrate in comparison with FIG. 8 and FIG. 9. FIG. 11 depicts the composite material of FIG. 10 at a magnification of 2000×, and clearly shows that the skin adhesive layer remains relatively unobstructed by the deposition product.

Figure 12:
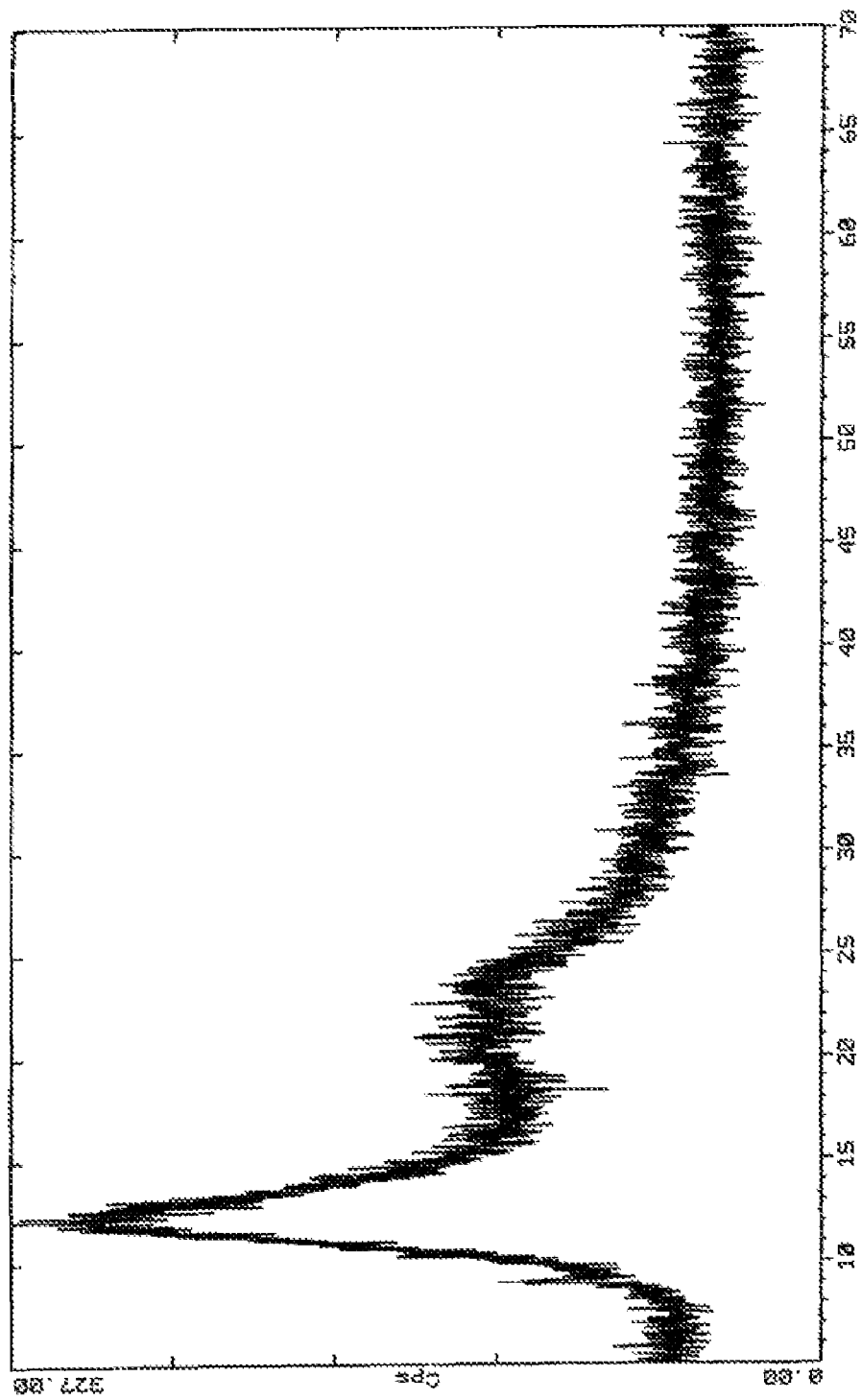
FIG. 12 is an XRD pattern generated from a substrate consisting of an uncoated sample of a perforated plastic carrier material with a skin adhesive layer comprised of a hydrophobic cross-linked silicon gel (trade-mark Mepitel™).
Figure 13:
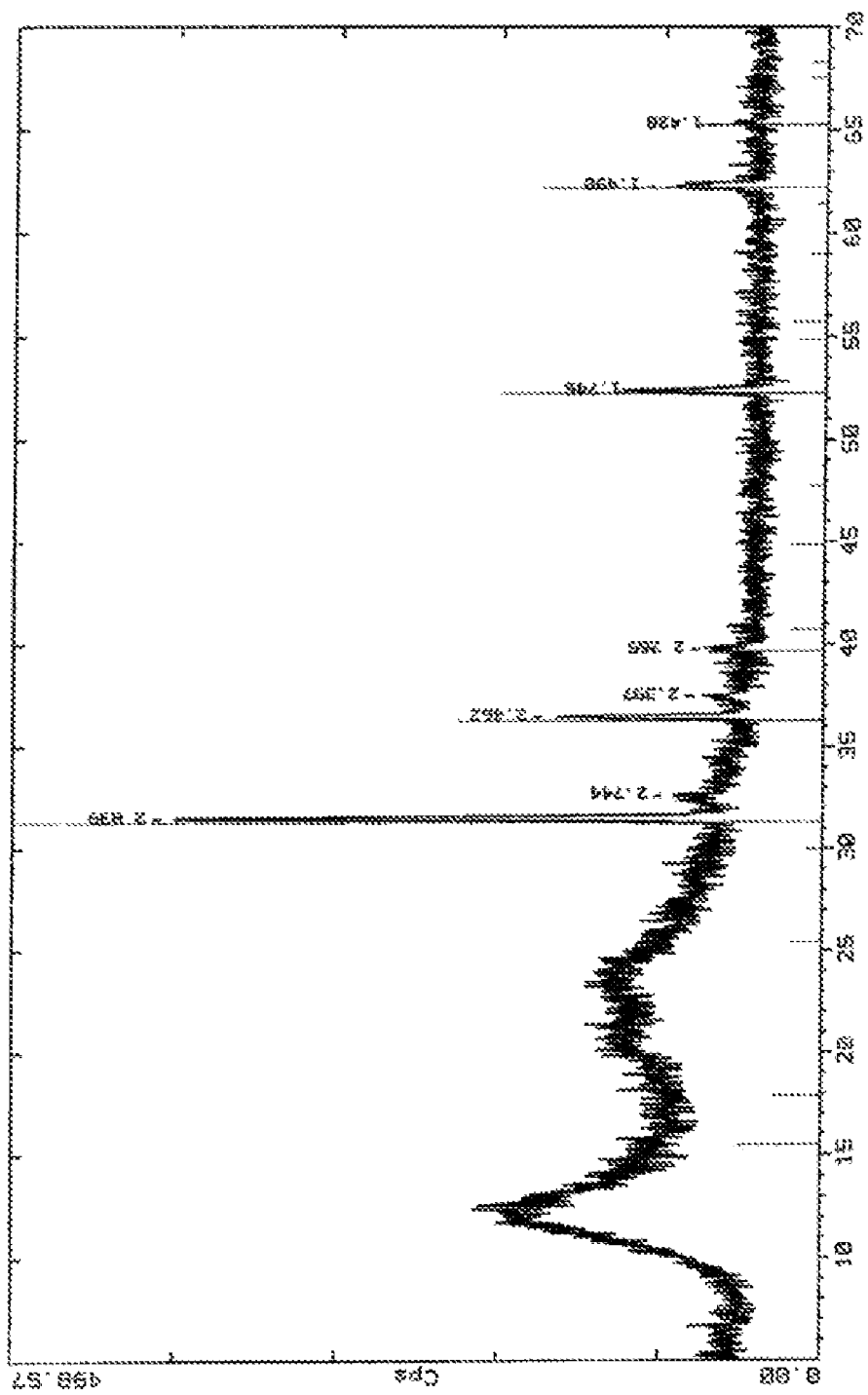
FIG. 13 is an XRD pattern generated from a composite material consisting of a coated sample of a perforated plastic carrier material with a skin adhesive layer comprised of a hydrophobic cross-linked silicon gel (trade-mark Mepitel™), in which a deposition product has been deposited on the substrate in accordance with the second and third aspects of the invention.
Figure 14:
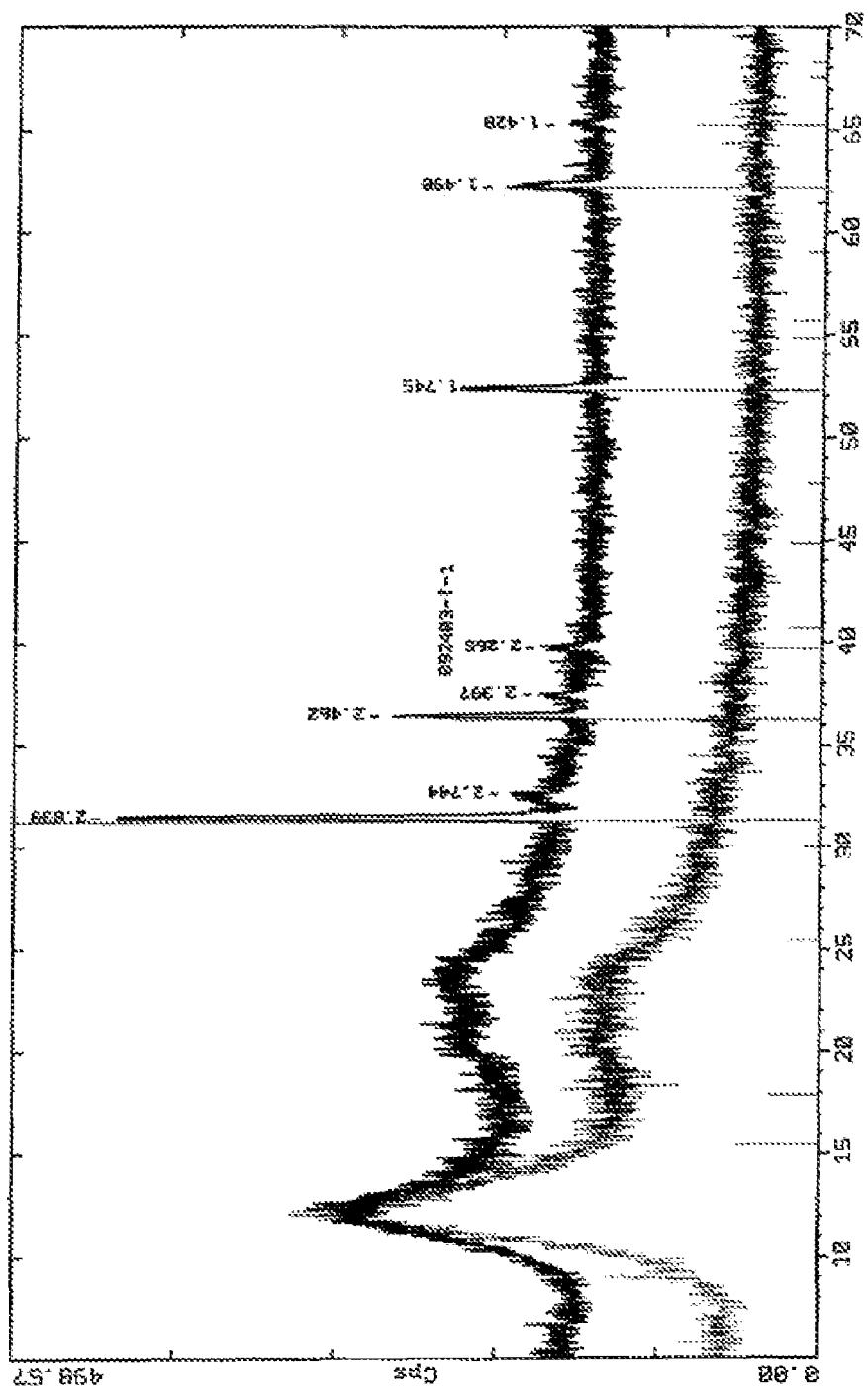
FIG. 14 is a superimposition of the XRD patterns depicted in FIG. 12 and FIG. 13.

FIG. 12 depicts an XRD pattern for an uncoated sample of the Mepitel™ wound dressing. FIG. 13 depicts an XRD pattern for a composite material comprising a sample of the Mepitel™ wound dressing which has been coated with a deposition product according to the second and third aspects of the invention in the same manner as described in Example 14. FIG. 14 superimposes the XRD patterns from FIG. 12 and FIG. 13.

Referring to FIG. 14, the peaks which are observed in the pattern from FIG. 13 but which are not observed in the pattern from FIG. 12 may be attributed to the deposition product. These peaks define the deposition product as comprising at least some amount of $Ag_7O_8NO_3$.

Example 18

Samples of a substrate consisting of a patterned wound dressing made of a perforated plastic carrier material with a skin adhesive layer comprised of a hydrophobic cross-linked silicon gel (trade-mark Mepitel™, product of Mölnlycke Health Care AB, Sweden) coated with 0.6 mg/cm2 of total silver according to the second and third aspects of the invention in the same manner as described in Example 14 were exposed to a solution containing 10 g/L $Na_2S$. After 10 minutes of exposure to the $Na_2S$ solution the coated wound dressing samples were carefully washed with water until pH 7.

After drying, the samples were tested for antimicrobial activity against *Pseudomonas aeruginosa* and *Staphylococcus aureus* using standard procedures. Clear zones of inhibition of bacterial growth surrounding test samples were observed for both *Pseudomonas aeruginosa* and *Staphylococcus aureus*, suggesting that a deposition product produced according to the second and third aspects of the invention will exhibit an antimicrobial activity even after exposure to a sulfide containing environment.

The embodiments of the invention in which an exclusive property or privilege is claimed are defined as follows:

1. A method for producing a deposition product, the method comprising the following steps:
   (a) providing a deposition solution comprising an amount of an aqueous solution of a silver salt comprised of an amount of silver ions and an amount of an oxidizing agent, wherein the silver salt is comprised of silver nitrate, wherein the oxidizing agent is comprised of a persulfate, wherein a concentration of the silver salt in the deposition solution is between about 1 gram per liter and about 20 grams per liter, wherein a concentration of the oxidizing agent in the deposition solution is between about 1 gram per liter and about 50 grams per liter, and wherein the deposition solution has a pH below 7; and
   (b) producing the deposition product by facilitating a chemical reaction in the deposition solution between the silver ions and the oxidizing agent while maintaining the deposition solution at a temperature of between about 2 degrees Celsius and about 40 degrees Celsius, wherein the deposition product consists essentially of at least one oxidized silver species, and wherein the deposition product is comprised of a compound having the formula $Ag_7O_8X$, where X is an anion.

2. The method as claimed in claim 1 wherein the persulfate is selected from the group of persulfates consisting of potassium persulfate, sodium persulfate, ammonium persulfate and mixtures thereof.

3. The method as claimed in claim 2 wherein the persulfate is comprised of potassium persulfate.

4. The method as claimed in claim 1 wherein the amount of the oxidizing agent is selected to be a stoichiometrically appropriate amount relative to the amount of the silver ions.

5. The method as claimed in claim 2, further comprising the step of adding an amount of a source of anions to the deposition solution for combining with the silver ions in order to produce the deposition product.

6. The method as claimed in claim 5 wherein the source of anions is comprised of at least one acid.

7. The method as claimed in claim 6 wherein the acid is selected from the group of acids consisting of carbonic acid, nitric acid, perchloric acid, sulfuric acid, acetic acid, fluoroboric acid, citric acid, acetylsalicylic acid and mixtures thereof.

8. The method as claimed in claim 5 wherein the amount of the source of anions is selected to be a stoichiometrically appropriate amount relative to the amount of the silver ions.

9. The method as claimed in claim 2 wherein the deposition product producing step is comprised of maintaining the deposition solution at a temperature of between about 10 degrees Celsius and about 25 degrees Celsius.

10. The method as claimed in claim 2 wherein the deposition product producing step is comprised of agitating the deposition solution during at least a portion of the deposition product producing step.

11. The method as claimed in claim 1 wherein the deposition product is further comprised of $Ag_2SO_4$.

12. The method as claimed in claim 1 wherein the deposition product is further comprised of at least one silver oxide selected from the group of silver oxides consisting of monovalent silver oxide, bivalent silver oxide, trivalent silver oxide and mixtures thereof.

13. The method as claimed in claim 1 wherein X is derived from an acid.

14. The method as claimed in claim 1 wherein the deposition product is comprised of a plurality of valent states of silver.

15. The method as claimed in claim 1 wherein X is selected from the group of anions consisting of $HCO_3^-$, $CO_3^{2-}$, $NO_3^-$, $ClO_4^-$, $SO_4^{2-}$, $F^-$, and mixtures thereof.

16. The method as claimed in claim 15 wherein X is comprised of $NO_3^-$.

* * * * *